(12) United States Patent
Dower et al.

(10) Patent No.: US 7,056,666 B2
(45) Date of Patent: Jun. 6, 2006

(54) ANALYSIS OF SURFACE IMMOBILIZED POLYMERS UTILIZING MICROFLUORESCENCE DETECTION

(75) Inventors: William J. Dower, Menlo Park, CA (US); Stephen P. A. Fodor, Palo Alto, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 10/077,070

(22) Filed: Feb. 14, 2002

(65) Prior Publication Data

US 2004/0029115 A9    Feb. 12, 2004

Related U.S. Application Data

(63) Continuation of application No. 08/829,893, filed on Apr. 2, 1997, now abandoned, which is a continuation of application No. 08/679,478, filed on Jul. 12, 1996, now Pat. No. 5,902,723, which is a continuation of application No. 07/626,730, filed on Dec. 6, 1990, now Pat. No. 5,547,839.

(51) Int. Cl.
C12Q 1/68 (2006.01)
C12P 19/34 (2006.01)
C07H 21/02 (2006.01)

(52) U.S. Cl. .................. 435/6; 435/91.1; 435/91.2; 536/23.1; 536/24.3

(58) Field of Classification Search .................. 435/6, 435/91.2; 536/23.1, 24.3
See application file for complete search history.

(56) References Cited

U.S. PATENT DOCUMENTS

| | | | |
|---|---|---|---|
| 3,849,137 A | 11/1974 | Barznski et al. | |
| 3,862,056 A | 1/1975 | Hartman | |
| 4,072,576 A | 2/1978 | Arwin et al. | |
| 4,238,757 A | 12/1980 | Schenk | |
| 4,314,821 A | 2/1982 | Rice | |
| 4,339,528 A | 7/1982 | Goldman | |
| 4,405,771 A | 9/1983 | Jagur | |
| 4,444,878 A | 4/1984 | Paulus | |
| 4,444,892 A | 4/1984 | Malmros | |
| 4,517,338 A | 5/1985 | Urdea et al. | |
| 4,542,102 A | 9/1985 | Dattagupta et al. | |
| 4,555,490 A | 11/1985 | Merril | |
| 4,562,157 A | 12/1985 | Lowe et al. | |
| 4,569,967 A | 2/1986 | Kornreich et al. | |
| 4,582,789 A | 4/1986 | Sheldon et al. | |
| 4,631,211 A | 12/1986 | Houghton | |
| 4,637,861 A | 1/1987 | Krull et al. | |
| 4,656,127 A | 4/1987 | Mundy | |
| 4,681,859 A | 7/1987 | Kramer | |
| 4,689,405 A | 8/1987 | Frank et al. | |
| 4,704,353 A | 11/1987 | Humphries et al. | |
| 4,713,326 A | 12/1987 | Dattagupta et al. | |
| 4,713,347 A | 12/1987 | Mitchell et al. | |
| 4,719,615 A | 1/1988 | Feyrer et al. | |
| 4,722,906 A | 2/1988 | Guire | |
| 4,762,881 A | 8/1988 | Kauer | |
| 4,777,019 A | 10/1988 | Dandekar | |
| 4,786,684 A | 11/1988 | Glass | |
| 4,794,150 A | 12/1988 | Steel | |
| 4,808,508 A | 2/1989 | Platzer | |
| 4,811,218 A * | 3/1989 | Hunkapiller et al. | ... 364/413.01 |
| 4,822,566 A | 4/1989 | Newman | |
| 4,833,092 A | 5/1989 | Geysen | |
| 4,851,331 A | 7/1989 | Vary et al. | |
| 4,855,225 A | 8/1989 | Fung et al. | |
| 4,865,990 A | 9/1989 | Stead et al. | |
| 4,889,818 A | 12/1989 | Gelfand et al. | |
| 4,946,942 A | 8/1990 | Fuller et al. | |
| 4,962,037 A | 10/1990 | Jett et al. | |
| 4,965,188 A | 10/1990 | Mullis et al. | |
| 4,973,493 A | 11/1990 | Guire | |
| 4,979,959 A | 12/1990 | Guire | |
| 5,002,867 A | 3/1991 | Macevicz | |
| 5,026,840 A | 6/1991 | Dattagupta et al. | |
| 5,075,216 A | 12/1991 | Innis et al. | |
| 5,126,239 A | 6/1992 | Livak et al. | |
| 5,143,854 A | 9/1992 | Pirrung et al. | |
| 5,202,231 A | 4/1993 | Drmanac | |
| 5,492,806 A | 2/1996 | Drmanac et al. | |
| 5,503,980 A | 4/1996 | Cantor | |
| 5,525,464 A | 6/1996 | Drmanac et al. | |
| 5,527,681 A | 6/1996 | Holmes | |
| 5,547,839 A * | 8/1996 | Dower et al. | ................ 435/6 |
| 5,631,134 A | 5/1997 | Cantor | |
| 5,667,972 A | 9/1997 | Drmanac et al. | |
| 5,695,940 A | 12/1997 | Drmanac et al. | |

(Continued)

FOREIGN PATENT DOCUMENTS

DE    2242394    3/1974

(Continued)

OTHER PUBLICATIONS

"Affymax raises $25 million to develop high-speed drug discovery system," *Biotechnology News*, 10(3):7-8 (1990).

(Continued)

*Primary Examiner*—Jeffrey Fredman
(74) *Attorney, Agent, or Firm*—Townsend and Townsend and Crew, LLP

(57) ABSTRACT

Means for simultaneous parallel sequence analysis of a large number of biological polymer macromolecules. Apparatus and methods may use fluorescent labels in repetitive chemistry to determine terminal manomers on solid phase immobilized polymers. Reagents which specifically recognize terminal manomers are used to label polymers at defined positions on a solid substrate.

15 Claims, 10 Drawing Sheets

U.S. PATENT DOCUMENTS

| | | | |
|---|---|---|---|
| 5,753,439 A | | 5/1998 | Smith et al. |
| 5,795,714 A | | 8/1998 | Cantor et al. |
| 5,807,522 A | | 9/1998 | Brown et al. |
| 5,849,878 A | | 12/1998 | Cantor et al. |
| 5,902,723 A | | 5/1999 | Dower et al. |
| 5,972,619 A | | 10/1999 | Drmanac |
| 6,007,987 A | | 12/1999 | Cantor et al. |
| 6,013,431 A | * | 1/2000 | Soderlund et al. .............. 435/5 |
| 6,018,041 A | | 1/2000 | Drmanac |
| 6,025,136 A | | 2/2000 | Drmanac |
| 6,054,270 A | | 4/2000 | Southern |

FOREIGN PATENT DOCUMENTS

| | | |
|---|---|---|
| DE | 3440141 | 5/1986 |
| EP | 088 636 | 9/1983 |
| EP | 127 438 | 12/1984 |
| EP | 245 662 | 11/1987 |
| EP | 288 310 | 10/1988 |
| EP | 319 012 | 6/1989 |
| EP | 328 256 | 8/1989 |
| EP | 373 203 B1 * | 11/1989 |
| EP | 392 546 | 10/1990 |
| EP | 416 817 A2 | 3/1991 |
| EP | 607 151 B1 | 11/2002 |
| GB | 2233654 A | 1/1991 |
| JP | 60-248699 A | 12/1985 |
| JP | 63-084499 A | 4/1988 |
| WO | WO 84/03564 | 9/1984 |
| WO | WO 86/00991 | 2/1986 |
| WO | WO 86/06487 | 11/1986 |
| WO | WO 89/10414 A1 | 11/1989 |
| WO | WO 89/10977 | 11/1989 |
| WO | WO 89/11548 | 11/1989 |
| WO | WO 89/12819 | 12/1989 |
| WO | WO 90/00887 | 2/1990 |
| WO | WO 90/03382 | 4/1990 |
| WO | WO 90/04652 | 5/1990 |
| WO | WO 90/09455 A1 | 8/1990 |
| WO | WO 90/11372 A1 | 10/1990 |
| WO | WO 90/13666 | 11/1990 |
| WO | WO 90/15070 | 12/1990 |
| WO | WO 91/04266 | 4/1991 |
| WO | WO 91/06678 | 5/1991 |
| WO | WO 91/07087 | 5/1991 |
| WO | WO 91/13075 A2 | 9/1991 |
| WO | WO 93/17126 | 9/1993 |
| WO | WO 95/09248 | 4/1995 |
| WO | WO 98/31836 | 7/1998 |

OTHER PUBLICATIONS

Ajayaghosh et al., "Solid-Phase Synthesis of N-Methyl- and N-Ethylamides of Peptides Using Photolytically Detachable ((3-Nitro-4((alkylamino)methyl)benzamido)methyl)polystyrene Resin," *J.Org.Chem.*, 55(9):2826-2829 (1990).

Ajayaghosh et al., "Solid-phase synthesis of C-terminal peptide amides using a photoremovable α-methylphenacylamido anchoring linkage," *Proc. Ind. Natl. Sci (Chem.Sci.)*, 100(5):389-396 (1988).

Ajayaghosh et al., "Polymer-supported Solid-phase Synthesis of C-Terminal Peptide N-Methylamides Using a Modified Photoremovable 3-Nitro-4-N-methylaminomethylpolystyrene Support," *Ind.J.Chem.*, 27B:1004-1008 (1988).

Ajayaghosh et al., "Polymer-Supported Synthesis of Protected Peptide Segments on a Photosensitive o-Nitro(α-Methyl)Bromobenzyl Resin," *Tetrahedron*, 44(21);6661-6666 (1988).

Amit et al., "Photosensitive Protecting Groups of Amino Sugars and Their Use in Glycoside Synthesis. 2-Nitrobenzyloxycarbonylamino and 6-Nitroveratryloxycarbonylamino Derivatives," *J.Org. Chem*, 39(2):192-196 (1974).

Applied Biosystems, Model 431A Peptide Synthesizer User's manual, Sections 2 and 6, (Aug. 15, 1989).

Atherton et al., Solid Phase Peptide Synthesis: A Practical Approach, IRL Press, (1989), tbl. of cont., pp. vii-ix.

Bains et al., "A Novel Method for Nucleic Acid Sequence Determination," *J.Theor.Biol.*, 135:303-307 (1988).

Bains, W., "Alternative Routes Through the Genome," *Biotechnology*, 8:1251-1256 (1988).

Balachander et al., "Functionalized Siloxy-Anchored Monolayers with Exposed Amino, Azido, Bromo, or Cyano Groups," *Tetrahed. Ltrs.*, 29(44):5593-5594 (1988).

Barinaga, M., "Will 'DNA Chip' Speed Genome Initiative," *Science*, 253:1489 (1985).

Baum, R., "Fledgling firm targets drug discovery process," *Chem. Eng. News*, p. 10-11 (1990).

Biorad Chromatography Electrophoresis Immunochemistry Molecular Biology HPLC catalog M 1987 pp. 182.

Carrano et al., "A High-Resolution, Fluorescence-Based, Semiautomated Method for DNA Fingerprinting," *Genomics*, 4:129-136 (1989).

Chatterjee et al., "Inducible Alkylation of DNA Using an Oligonucleotide-Quinone Conjugate," *Am. J. Chem. Soc.*, 112:6397-6399 (1990).

Chetverin et al., "Oligonucleotide Arrays: New Concepts and Possibilities," *Biotechnology*, 12:1093-1099 (1994).

Chidgeavadze et al., "2', 3'-Dieoxy-3' aminonucleoside 5'-triphosphates are the terminators of DNA synthesis catalyzed by DNA polymerases," *Nuc. Acids Res.*, 12(3):1671-1686 (1984).

Chidgeavadze et al., "3'-Fluoro-2', 3'-dideoxyribonucleoside 5'- triphosphates: Terminators of DNA synthesis," *FEBS Letters*, 183(2):275-278 (1985).

Chien et al., "Deoxyribonucleic Acid Polymerase from the Extreme Thermophile Thermus aquaticus," *J. Bacteriol.*, 127:1550-1557 (1976).

Cimino et al., "Psoralens as Photoactive Probes of Nucleic Acid Structure and Function: Organic Chemistry, Photochemistry and Biochemistry," *Ann. Rev. Biochem.*, 54:1151-1193 (1985).

Corbett et al., "Reaction of Nitroso Aromatics with Glyoxylic Acid. A New Path to Hydroxamic Acids," *J. Org. Chem.*, 45:2834-2839 (1980).

Coulson et al., "Toward a physical map of the genome of the nematode *Caenorhabditis elegans*," *PNAS*, 83:7821-7825 (1986).

Craig et al., "Ordering of cosmid clones covering the Herpes simplex virus type I (HSV-1) genome: a test case for fingerprinting by hybridization," *Nuc. Acid. Res.*, 18(9):2653-2660 (1990).

Dower et al., "The Search for Molecular Diversity (II): Recombinant and Synthetic Randomized Peptide Libraries," *Ann. Rep. Med. Chem.*, 26:271-280 (1991).

Drmanac et al., "Subfragments as an informative characteristic of the DNA molecule—computer simulation," thesis submitted to University of Belgrade College of Natural Sciences and Mathematics, (1988).

Drmanac et al., "Partial Sequencing by Oligo-Hybridization Concept and Applications in Genome Analysis," *1st Int. Conf. Electrophor., Supercomp., Human Genome*, pp. 60-74 (1990).

Drmanac et al., "Sequencing by Oligonucleotide Hybridization: A Promising Framework in Decoding of the Genome Program?," *1st Intl. Conf. Electrophor., Supercomp., Human Genome*, pp. 47-59 (1990).

Drmanac et al., "Laboratory Methods, Reliable Hybridization of Oligonucleotides as Short as Six Nucleotides," *DNA and Cell Biol.*, 9(7):527-534 (1990).

Drmanac et al., "Sequencing of Megabase Plus DNA by Hybridization: theory of the Method," *Genomics*, 4:114-128 (1989).

Dulcey et al., "Deep UV Photochemistry of Chemisorbed Monolayers: Patterned Coplanar Molecular Assemblies," *Science*, 252:551-554 (1991).

Duncan et al., "Affinity Chromatography of a Sequence-Specific DNA Binding Protein Using Teflon-Linked Oligonucleotides," *Analytical Biochemistry*, 169:104-108 (1988).

Evans et al., "Physical mapping of complex genomes by cosmid multiplex analysis," *PNAS*, 86:5030-5034 (1989).

Flanders et al., "A new interferometric alignment technique," *App. Phys. Ltrs.*, 31(7):426-429 (1977).

Fodor et al., "Light-directed, Spatially Addressable Parallel Chemical Synthesis," *Science*, 251:767-773 (1991).

Frank et al., "Simultaneous Multiple Peptide Synthesis Under Continuous flow Conditions on Cellulose Paper Discs as Segmental Solid Supports," *Tetrahedron*, 44(19):6031-6040 (1988).

Frank et al., "Automation of DNA Sequencing Reactions and Related Techniques: A Workstation for Micromanipulation of Liquids," *Bio/Technology*, 6:1211-1212 (1988).

Fuller et al., "Urethane-Protected Amino Acid N-Carboxy Anhydrides and Their Use in Peptide Synthesis," *J. Amer. Chem. Soc.*, 112(20):7414-7416 (1990).

Furka et al., "General method for rapid synthesis of multicomponent peptide mixtures," *Int. J. Peptide Protein Res.*, 37:487-493 (1991).

Furka et al., "Comucopia of Peptides by Synthesis," 14th int. Congress of Biochem. abst.# FR:013, Jul. 10-15, 1988 Prague, Czechoslovakia.

Furka et al., "More Peptides by Less Labour," abst. 288, Int. Symp. Med. Chem., Budapest Hungary Aug. 15-19, 1988.

Gait, eds., pp. 1-115 from *Oligonucleotide Synthesis: A Practical Approach*, IRL Press, (1984).

Gazard et al., "Lithographic Technique Using Radiation-Induced Grafting of Acrylic Acid into Poly(Methyl Methacrylate) Films," *Polymer Engineering and Science*, 20(16):1069-1072 (1980).

Gerard et al., "Influence on stability in *Eschcrichia coli* of the carboxy-terminal structure of cloned Moloney murine leukemia virus reverse transcriptase," *DNA*, 5(4):271-279 (1986).

Getzoff et al., "Mechanisms of Antibody Binding to a Protein," *Science*, 235:1191-1196 (1987).

Geysen et al., "Strategies for epitope analysis using peptide synthesis," *J. Immunol. Meth.*, 102:259-274 (1987).

Geysen et al., "Use of peptide synthesis to probe viral antigens for epitopes to a resolution of a single amino acid," *PNAS*, 81:3998-4002 (1984).

Geysen et al., "A synthetic strategy for epitope mapping," from Peptides:Chem & Biol., Proc. of 10th Am. Peptide Symp., May 23-28, 1987, pp. 519-523, (1987).

Geysen, "Antigen-antibody interactions at the molecular level: adventures in peptide synthesis," *Immunol. Today*, 6(12):364-369 (1985).

Geysen et al., "Chemistry of Antibody Binding to a Protein," *Science*, 235:1184-1190 (1987).

Geysen et al., "The delineation of peptides able to mimic assembled epitopes," 1986 CIBA Symp., pp. 130-149.

Geysen et al., "Cognitive Features of Continuous Antigenic Determinants," *Mol. Recognit.*, 1(1):1-10 (1988).

Geysen et al., "A Prio Ri Delineation of a Peptide Which Mimics A Discontinuous Antigenic Determinant," *Mol. Immunol.*, 23(7):709-715 (1986).

Geysen et al., *Synthetic Peptides: Approaches to Biological Probes*, Alan R. Liss, Inc., pp. 19-20 (1989).

Haridasan et al., "Peptide Synthesis using Photolytically Cleavable 2-Nitrobenzyloxycarbonyl Protecting Group," *Proc. Indian Natn. Sci. Adad.*, 53A(6):717-728 (1987).

Ho et al., "Highly Stable Biosensor Using an Artificial Enzyme," *Anal.Chem.*, 59:536-537 (1987).

Houts et al., "Reverse Transcriptase from Avian Myeloblastosis Virus," *J. Virol.*, 29(2):517-522 (1979).

Ikehara et al., "The synthesis of Polynucleotides," *Advances in Carbohydrate Chem. & Biochem.*, 36:135-213 (1979).

Innis et al., "DNA sequencing with *Thermus aquaticus* DNA polymerase and direct sequencing of polymerase chain reaction-amplified DNA," *PNAS*, 85:9436-9440 (1988).

Jacobsen et al., "The N-terminal amino-acid sequences of DNA polymerase I from *Escherichia coli* and of the large and the small fragments obtained by a limited proteolysis," *Eur. J. Biochem.*, 45(2):623-627 (1974).

Kaiser et al., "Peptide and Protein Synthesis by Segment Synthesis-Condensation," *Science*, 243:187-192 (1989).

Kambra et al., "Optimization of Parameters in a DNA Sequenator Using Fluorescence Detection," *Bio/Tech*, 6:816-821 (1988).

Karube, "Micro-biosensors based on silicon fabrication technology," chapter 25 from Biosensors:Fundamentals and Applications, Turner et al., eds., Oxford Publ., 1987, pp. 471-480 (1987).

Khrapko et al., "An Oligonucleotide hybridization approach to DNA sequencing," *FEBS Lett.*, 256(1,2):118-122 (1989).

Klenow et al., "Selective Elimination of the Exonuclease Activity of the Deoxyribonucleic Acid Polymerase from *Escherichia coli* B by Limited Proteolysis," *PNAS*, 65(2):168-175 (1970).

Knight, P., "Materials and Methods/Microsequencers for Proteins and Oligosaccharides," *Bio/Tech.*, 7:1075-76 (1989).

Kotewicz et al., "Cloning and overexpression of Moloney murine leukemia virus reverse transcriptase in *Escherichia coli,"* Gene, 85:249-258 (1985).

Kutateladze et al., "Analogs of nucleoside triphosphates with modified sugar residues as substrates for RNA polymerase," *Molekulyarnaya Biologiya*, 20(1):267-277 (1986).

Lee et al., "synthesis of a Polymer Surface Containing Covalently Attached Triethoxysilane Functionality: Adhesion to Glass," *Macromolecules*, 21:3353-3356 (1988).

Levy, M.F., "Preparing Additive Printed Circuits," *IBM Tech. Discl. Bull.*, 9(11):1473 (1967).

Lieberman et al., "A Light source Smaller Than the Optical Wavelength," *Science*, 247:59-61 (1990).

Little, P., "Clone maps made simple," *Nature*, 346:611-612 (1990).

Lowe, C.R., "Biosensors," *Trends in Biotech.*, 2:59-65 (1984).

Lowe, C.R., "An Introduction to the Concepts and Technology of Biosensors," *Biosensors*, 1:3-16 (1985).

Lowe, C. R., Biotechnology and Crop Improvement and Protection, BCPC Publications, pp. 131-138 (1986).

Lowe et al., "Solid-Phase Optoelectronic Biosensors," *Methods in Enzymology*, 137:338-347 (1988).

Lowe, C.R., "Biosensors," *Phil. Tran. R. Soc. Lond.*, 324:487-496 (1989).

Lysov et al., "A new method for determining the DNA nucleotide sequence by hybridization with oligonucleotides," *Doklady Biochem.*, 303(1-6):436-438 (1989).

Maxam et al., "Sequencing End-Labeled DNA with Base-Specific Chemical Cleavages," *Meth. Enzymol.*, 65:499-560 (1980).

McCray et al., "Properties and Uses of Photoreactive Caged Compounds," *Ann. Rev. Biophys. Biophys. Chem.*, 18:239-270 (1989).

McGillis, VLSI Technology, Sze, eds., Chapter 7, "Lithography," pp. 267-301 (1983).

Merrifield, R.B., "Solid Phase peptide Synthesis. I. The Synthesis of a Tetrapeptide," *J.Am.Chem.Soc.*, 85:2149-2154 (1963).

Michiels et al., "Molecular approaches to genome analysis: a strategy for the construction of ordered overlapping clone libraries" *CABIOS*, 3(3):203-10 (1987).

Morita et al., "Direct pattern fabrication on silicone resin by vapor phase electron beam polymerization," *J.Vac.Sci. Technol.*, B1(4):1171-1173 (1983).

Nelson et al., "A new and versatile reagent for incorporating multiple primary aliphatic amines into synthetic oligonucleotides," *Nuc. Acids Res.*, 17(18):7179-7186 (1989).

Nossal, N.G., "DNA synthesis on a Double-stranded DNA template by the T4 Bacteriophage DNA polymerase and the T4 Gene 32 DNA Unwinding Protein," *J.Biol. Chem.*, 249(17):5668-5676 (1974).

Ohtsuka et al., "Studies on transfer ribonucleic acids and related compounds. IX Ribonucleic oligonucleotide synthesis using a photosensitive 0-nitrobenzyl protection at the 2' -hydroxl group," *Nuc.Acids.Res.*1(10):1351-1357 (1974).

Olson et al., "Random-clone strategy for genomic restriction mapping in yeast," *PNAS*, 83:7826-7830 (1986).

Parsons, B.J., "Psoralen Photochemistry," *Photochem. Photobiol.*, 32:813-821 (1980).

Patchornik et al., "Photosensitive Protecting Groups," *J.Am. Chem.Soc.*, 92(21):6333-6335 (1970).

Pevzner, P.A., "1-Tuple DNA Sequencing: Computer Analysis," *J. Biomol. Struct. Dynam.*, 7(1):63-69 (1989).

Pfeifer et al., "Genomic Sequencing and Methylation Analysis by Ligation Mediated PCR," *Science*, 246:810-813 (1989).

Pidgeon et al., "Immobilized Artificial Membrane Chromatography: Supports Composed of Membrane Lipids," *Anal. Biochem.*, 176:36-47 (89).

Poustka et al., "Molecular Approaches to Mammalian Genetics," Cold Spring Harbor Symposia on Quantitive Biology, 51:131-139 (1986).

Prober et al., "A System for Repid DNA Sequencing with Fluorescent Chain-Terminating Dieoxynucleotides," *Science*, 238:336-341 (1987).

Purushothaman et al., "Synthesis of 4,5-diarylimidazoline-2-thiones and their photoconversion to bis(4,5-diarylimidazol-2-yl) sulphides," *Ind. J. Chem.*, 29B:18-21 (1990).

Roberts, L., "A Sequencing Reality Check," *Science*, 242:1245 (1988).

Rodda et al., "The Antibody Response to Myoglobin-I. Systematic Synthesis of Myglobin Peptides Reveals Location and Substructure of Species-Dependent Continuous Antigenic Determinants," *Mol. Immunol.*, 23(6):603-610 (1986).

Ross et al., "Interstrand Crosslinks due to 4, 5', 8-trimethylpsoralen and Near Ultraviolet Light in Specific Sequences of Animal DNA," *J. Mol. Biol.*, 201:339-351 (1988).

Ruth et al., "Nucleoside Analogues with Clinical Potential in Antivirus Chemotherapy," *Mol. Pharm.*, 20:415-422 (1981).

Saiki et al., "Introducing AmpliTaq DNA polymerase," *Amplifications*, 1:4-6 (1989).

Sanger et al., "A Rapid Method for Determining Sequences in DNA by Primed Synthesis with DNA Polymerase," *J. Mol. Biol.*, 94:441-448 (1975).

Sanger et al., "DNA sequencing with chain-terminating inhibitors," *PNAS*, 74(12):5463-5467 (1977).

Second College edition of the American Heritage Dictionary, p. 522.

Seed, B., "Diazotizable arylamine cellulose papers for the coupling and hybridization of nucleic acids," *Nuc. Acids Res.*, 10(5):1799-1810 (1982).

Smith et al., "The synthesis of oligonucleotides contianing an aliphatic amino group at the 5' terminus: Synthesis of fluorescent DNA primers for use in DNA sequence analysis," *Nuc. Acids Res.*, 13(7):2399-2412 (1985).

Smith et al., "Fluorescence detection in automated DNA sequence analysis," *Nature*, 321:674-679 (1986).

Smith et al., "A Novel Method for Delineating Antigenic Determinants: Peptide Synthesis and Radioimmunoassay Using the Same Solid Support," *Immunochemistry*, 14:565-568 (1977).

Song et al., "Photochemistry and photobiology of psoralens," *Photochem. Photobiol.*, 29:1177-1197 (1979).

Steuber et al., "Synthesis and Photolytic Cleavage of Bovine Insulin B22-30 on a Nitrobenzoylglycyl-polyethylene glycol support," *Chemical abstracts*, 100(17):700, abstract No. 139591v (1984).

Stuber et al., "Synthesis and photolytic cleavage of bovine insulin $B_{22-30}$ on a nitrobenzoylglycyl-poly (ethylene glycol) support," *Intl. J. Peptide Protein Res.*, 22:277-283 (1983).

Tabor et al., "Selective Oxidation of the Exonuclease Domain of Bacteriophage T7 DNA Polymerase," *J. Biol. Chem.*, 262(32):15330-15333 (1987).

Tabor et al., "DNA sequence analysis with a modified bacteriophage T7 DNA polymerase," *PNAS*, 84:4767-4771 (1987).

Tsugita et al., "Sensitization of Edman Amino Acid Derivatives Using the Fluorescent Reagent 4-Aminofluorescein," *J. Biochem.*, 106:60-65 (1989).

Turner et al., "Photochemical Activation of Acylated α-Thrombin," *J. Am. Chem. Soc.*, 109:1274-1275 (1987).

Weising et al., "Foreign genes in plants: Transfer, structure, expression, and applications," *Annu. Rev. Genet.*, 22:421-477 (1988).

Wiesehahn et al., "DNA unwinding induced by photoaddition of psorlaen derivatives and determination of dark binding equilibrium constants by gel electrophoresis," *PNAS*, 75:2703-2707 (1978).

Wittman-Liebold, eds., Methods in Protein Sequence Analysis, from Proceedings of the 7th Int'l Conf., Berlin, Germany, Jul. 3-8, 1988, table of contents, pp. xi-xx* (1989).

Wood et al., "Base composition-independent hybridization in tetramethylammonium chloride: A method for oligonucleotide screening of highly complex gene libraries," *PNAS*, 82:1585-1588 (1985).

Ye et al., "Heat-stable DNA polymerase I large fragment resolves hairpin structure in DNA sequencing," *Scientia Sinica (Series B)*, 30(5):503-506 (1987).

Yosomiya et al., "Performance, Glass fiber Having Isocyanate Group on the Surface. Preparation and Reaction with Amino Acid," *Polymer Bulletin*, 12:41-48 (1984).

Zehavi et al., "Light-Sensitive Glycosides. I. 6-Nitroveratryl β-D-Glucopyranoside and 2-Nitrobenzyl β-D-Glucopyranoside," *J. Org. Chem.*, 37(14):2281-2285 (1972).

* cited by examiner

PATHWAY TO PROTECTED NUCLEOTIDES

PREFERRED PATHWAY TO BASE PROTECTION AND FUNCTIONALIZATION

US 7,056,666 B2

ANALYSIS OF SURFACE IMMOBILIZED POLYMERS UTILIZING MICROFLUORESCENCE DETECTION

The present application is a continuation of U.S. Ser. No. 08/829,893, filed Apr. 2, 1997 (now abandoned), which is a continuation of U.S. Ser. No. 08/679,478 (now U.S. Pat. No. 5,902,723), filed Jul. 12, 1996, which is a continuation of U.S. Ser. No. 07/626,730 (now U.S. Pat. No. 5,547,839), filed Dec. 6, 1990.

BACKGROUND OF THE INVENTION

The present invention relates to the determination of the sequences of polymers immobilized to a substrate. In particular, one embodiment of the invention provides a method and apparatus for sequencing many nucleic acid sequences immobilized at distinct locations on a matrix surface. The principles and apparatus of the present invention may be used, for example, also in the determination of sequences of peptides, polypeptides, oligonucleotides, nucleic acids, oligosaccharides, phospholipids and other biological polymers. It is especially useful for determining the sequences of nucleic acids and proteins.

The structure and function of biological molecules are closely interrelated. The structure of a biological polymer, typically a macromolecule, is generally determined by its monomer sequence. For this reason, biochemists historically have been interested in the sequence characterization of biological macromolecule polymers. With the advent of molecular biology, the relationship between a protein sequence and its corresponding encoding gene sequence is well understood. Thus, characterization of the sequence of a nucleic acid encoding a protein has become very important.

Partly for this reason, the development of technologies providing the capability for sequencing enormous amounts of DNA has received great interest. Technologies for this capability are necessary for, for example, the successful completion of the human genome sequencing project. Structural characterization of biopolymers is very important for further progress in many areas of molecular and cell biology.

While sequencing of macromolecules has become extremely important, many aspects of these technologies have not advanced significantly over the past decade. For example, in the protein sequencing technologies being applied today the Edman degradation methods are still being used. See, e.g., Knight (1989) "Microsequencers for Proteins and Oligosaccharides," *Bio/Technol.* 7:1075–1076. Although advanced instrumentation for protein sequencing has been developed, see, e.g., Frank et al. (1989) "Automation of DNA Sequencing Reactions and Related Techniques: A Work Station for Micromanipulation of Liquids," *Bio/Technol.* 6:1211–1213, this technology utilizes a homogeneous and isolated protein sample for determination of removed residues from that homogeneous sample.

Likewise, in nucleic acid sequencing technology, three major methods for sequencing have been developed, of which two are commonly used today. See, e.g., Sambrook et al. (1989) *Molecular Cloning: A Laboratory Manual* (2d Ed.) Vols. 1–3, Cold Spring Harbor Press, New York, which is hereby incorporated herein by reference. The first method was developed by Maxam and Gilbert. See, e.g., Maxam and Gilbert (1980) "Sequencing End-Labeled DNA with Base-Specific Chemical Cleavages," *Methods in Enzymol.* 65:499–560, which is hereby incorporated herein by reference. The polymer is chemically cleaved with a series of base-specific cleavage reagents thereby generating a series of fragments of various lengths. The various fragments, each resulting from a cleavage at a specific base, are run in parallel on a slab gel which resolves nucleic acids which differ in length by single nucleotides. A protein specific label allows detection of cleavages at all nucleotides relative to the position of the label.

This separation requires high resolution electrophoresis or some other system for separating nucleic acids of very similar size. Thus, the target nucleic acid to be sequenced must usually be initially purified to near homogeneity.

Sanger and Coulson devised two alternative methods for nucleic acid sequencing. The first method, known as the plus and minus method, is described in Sanger and Coulson (1975) *J. Mol. Biol.* 94:441–448, and has been replaced by the second method. Subsequently, Sanger and Coulson developed another improved sequencing method known as the dideoxy chain termination method. See, e.g., Sanger et al. (1977) "DNA Sequencing with Chain-Termination Inhibitors," *Proc. Natl. Acad. Sci. USA* 74:5463–5467, which is hereby incorporated herein by reference. This method is based on the inability of 2', 3' dideoxy nucleotides to be elongated by a polymerase because of the absence of a 3' hydroxyl group on the sugar ring, thus resulting in chain termination. Each of the separate chain terminating nucleotides are incorporated by a DNA polymerase, and the resulting terminated fragment is known to end with the corresponding dideoxy nucleotide. However, both of the Sanger and Coulson sequencing techniques usually require isolation and purification of the nucleic acid to be sequenced and separation of nucleic acid molecules differing in length by single nucleotides.

Both the polypeptide sequencing technology and the oligonucleotide sequencing technologies described above suffer from the requirement to isolate and work with distinct homogeneous molecules in each determination.

In the polypeptide technology, the terminal amino acid is sequentially removed and analyzed. However, the analysis is dependent upon only one single amino acid being removed, thus requiring the polypeptide to be homogeneous.

In the case of nucleic acid sequencing, the present techniques typically utilize very high resolution polyacrylamide gel electrophoresis. This high resolution separation uses both highly toxic acrylamide for the separation of the resulting molecules and usually very high voltages in running the electrophoresis. Both the purification and isolation techniques are highly tedious, time consuming and expensive processes.

Thus, a need exists for the capability to simultaneously sequence many biological polymers without individual isolation and purification. Moreover, dispensing with the need to individually perform the high resolution separation of related molecules leads to greater safety, speed, and reliability. The present invention solves these and many other problems.

SUMMARY OF THE INVENTION

The present invention provides the means to sequence hundreds, thousands or even millions of biological macromolecules simultaneously and without individually isolating each macromolecule to be sequenced. It also dispenses with the requirement, in the case of nucleic acids, to separate the products of the sequencing reactions on dangerous polyacrylamide gels. Adaptable to automation, the cost and effort required in sequence analysis will be dramatically reduced.

This invention is most applicable, but not limited, to linear macromolecules. It also provides specific reagents for sequencing both oligonucleotides and polypeptides. It provides an apparatus for automating the processes described herein.

The present invention provides methods for determining the positions of polymers which terminate with a given monomer, where said polymers are attached to a surface having a plurality of positionally distinct polymers attached thereto, said method comprising the steps of:

labeling a terminal monomer in a monomer type specific manner; and scanning said surface, thereby determining the positions of said label. In one embodiment, the polymers are polynucleotides, and usually the labeling of the terminal marker comprises incorporation of a labeled terminal monomer selected from the group of nucleotides consisting of adenine, cytidine, guanidine and thymidine.

An alternative embodiment provides methods for concurrently determining which subset of a plurality of positionally distinct polymers attached to a solid substrate at separable locations terminates with a given terminal subunit, said method comprising the steps of:

mixing said solid substrate with a solution comprising a reagent, which selectively marks positionally distinct polymers which terminate with said given terminal subunit; and determining with a detector which separable locations are marked, thereby determining which subset of said positionally distinct polymers terminated with said given terminal subunit. In one version, the solution comprises a reagent which marks the positionally distinct polymer with a fluorescent label moiety. In another version the terminal subunit is selected from the group consisting of adenosine, cytosine, guanosine, and thymine.

Methods are also provided for determining which subset of a plurality of primer polynucleotides have a predetermined oligonucleotide, wherein the polynucleotides are complementary to distinctly positioned template strands which are attached to a solid substrate, said method comprising the steps of:

selectively marking said subset of primer polynucleotides having the predetermined oligonucleotide; and detecting which polynucleotides are marked. In one embodiment, the oligonucleotide subunit is a single nucleotide; in another the marking comprises elongating said primer with a labeled nucleotide which is complementary to a template; and in a further embodiment the marking step uses a polymerase and a blocked and labeled adenine.

The invention embraces methods for concurrently obtaining sequence information on a plurality of polynucleotides by use of a single label detector, said method comprising the steps of:

attaching a plurality of positionally distinct polynucleotides to a solid substrate at separable locations;

labeling said plurality of polynucleotides with a terminal nucleotide specific reagent, said label being detectable using said label detector;

determining whether said specific labeling reagent has labeled each separable location. Often, the labeling is performed with reagents which can distinguishably label alternative possible nucleotide monomers. One embodiment uses four replica substrates each of which is labeled with a specific labeling reagent for adenine, cytosine, guanine, or thymine. Usually, the labeling and determining steps are performed in succession using reagents specific for each of adenine, cytosine, guanine, and thymine monomers.

An alternative embodiment provides methods for concurrently obtaining sequence information on a plurality of polynucleotides, said method comprising the steps of:

attaching distinct polynucleotides to a plurality of distinct solid substrates;

labeling said plurality of solid substrates with a terminal nucleotide specific labeling reagent; and determining whether said specific labeling reagent has labeled each distinct substrate. The method can be performed using in a continuous flow of distinct solid substrates through a reaction solution.

A method is provided for simultaneously sequencing a plurality of polymers made up of monomer units, said plurality of polymers attached to a substrate at definable positions, said method comprising the steps of:

mixing said substrate with a reagent which specifically recognizes a terminal monomer, thereby providing identification among various terminal monomer units; and scanning said substrate to distinguish signals at definable positions on said substrate; and correlating said signals at defined positions on said substrate to provide sequential series of sequence determinations. Often, the plurality of polymers are synthesized by a plurality of separate cell colonies, and the polymers may be attached to said substrate is by a carbonyl linkage. In one embodiment, the polymers are polynucleotides, and often the substrate comprises silicon. The scanning will often identify a fluorescent label. In one embodiment, the reagent exhibits specificity of removal of terminal monomers, in another, the reagent exhibits specificity of labeling of terminal monomers.

The invention also embraces methods for sequencing a plurality of distinctly positioned polynucleotides attached to a solid substrate comprising the steps of:

hybridizing complementary primers to said plurality of polynucleotides;

elongating a complementary primer hybridized to a polynucleotide by adding a single nucleotide; and identifying which of said complementary primers have incorporated said nucleotide. In some versions, the elongating step is performed simultaneously on said plurality of polynucleotides linked to said substrate. Typically, the substrate is a two dimensional surface and the identifying results from a positional determination of the complementary primers incorporating the single defined nucleotide. A silicon substrate is useful in this method.

Methods, are provided where the linking is by photo-crosslinking polynucleotide to said complementary primer, where said primer is attached to said substrate. The elongating will be often catalyzed by a DNA dependent polymerase. In various embodiments, a nucleotide will have a removable blocking moiety to prevent further elongation, e.g., NVOC.

A nucleotide with both a blocking moiety and labeling moiety will be often used.

A further understanding of the nature and advantages of the invention herein may be realized by reference to the remaining portions of the specification and the attached drawings.

BRIEF DESCRIPTION OF THE FIGURES

FIG. 8A illustrates schematically, at a molecular level, the sequence of events which occur during a particular sequencing cycle. FIG. 8B illustrates, in a logic flow chart, how the scheme is performed.

FIG. 10A illustrates schematically, at a molecular level, the sequence of events which occur during a particular sequencing cycle. FIG. 10B illustrates in a logic flow chart how the scheme is performed.

DETAILED DESCRIPTION OF THE PREFERRED EMBODIMENTS

Figure 1:
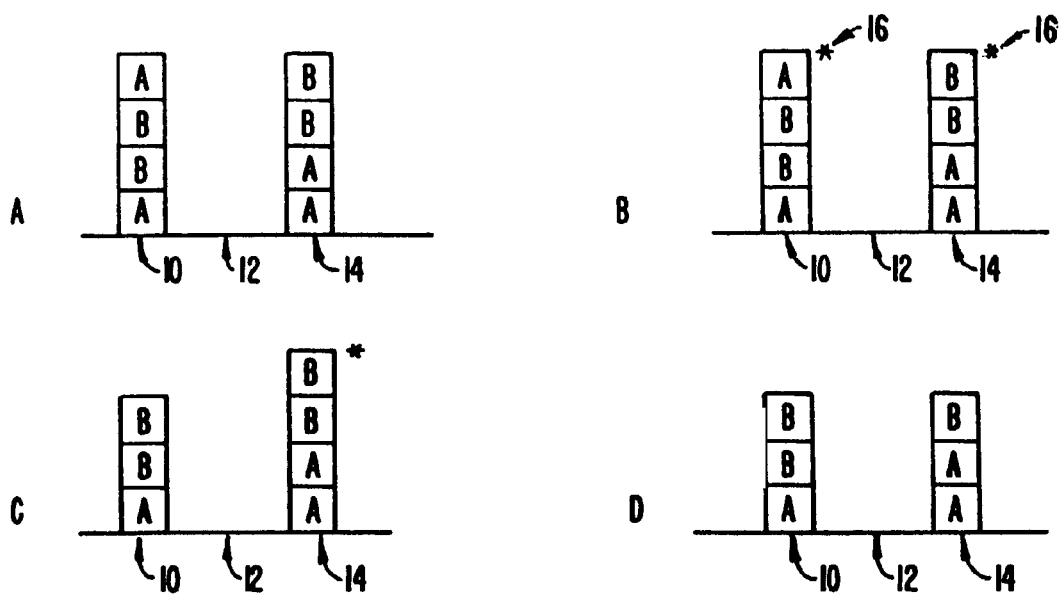
FIG. 1 illustrates a simplified and schematized embodiment of a degradative scheme for polymer sequencing.

I. Sequencing Procedure for a Generic Polymer
  A. Overview
    1. Substrate and matrix
    2. Scanning system
    3. Synthetic/degradative cycles
    4. Label
    5. Utility
  B. Substrate/Matrix
    1. Non-distortable
    2. Attachment of polymer
  C. Scanning system
    1. Mapping to distinct position
    2. Detection system
    3. Digital or analog signal
  D. Synthetic or degradative cycle
    1. Synthetic cycles
      a. synthetic scheme
      b. blocking groups
    2. Degradative cycles
    3. Conceptual principles
  E. Label
    1. Attachment
    2. Mode of detection
  F. Utility II. Specific Embodiments
  A. Synthetic method
  B. Chain degradation method
III. Apparatus I. Sequencing Procedure for a Generic Polymer The present invention provides methods and apparatus for the preparation and use of a substrate having a plurality of polymers with various sequences where each small defined contiguous area defines a small cluster of homogeneous polymer sequences. The invention is described herein primarily with regard to the sequencing of nucleic acids but may be readily adapted to the sequencing of other polymers, typically linear biological macromolecules. Such polymers include, for example, both linear cyclical polymers or nucleic acids, polysaccharides, phospholipids, and peptides having various different amino acids, heteropolymers in which the polymers are mixed, polyurethanes, polyesters, polycarbonates, polyureas, polyamides, polyethyleneimines, polyarylene sulfides, polysiloxanes, polyimides, polyacetates or mixed polymers of various sorts. In a preferred embodiment, the present invention is described in the use of sequencing nucleic acids.

Various aspects of U.S. Ser. No. 07/362,901, (VLSIP® parent); U.S. Ser. No. 07/492,462 (now U.S. Pat. No. 5,143,854) (VLSIP® CIP); U.S. Ser. No. 07/435,316 (caged biotin parent); U.S. Ser. No. 07/612,671 (now U.S. Pat. No. 5,252,743)(caged biotin CIP); and simultaneously filed cases U.S. Ser. No. 07/624,120, a divisional of which has issued as U.S. Pat. No. 5,744,101 (automated VLSIP®); and U.S. Ser. No. 07/624,114, a grandchild of which has issued as U.S. Pat. No. 5,800,992 (sequencing by hybridization); each of which is hereby incorporated by reference, are applicable to the substrates and matrix materials described herein, to the apparatus used for scanning the matrix arrays, to means for automating the scanning process, and to the linkage of polymers to a substrate.

By use of masking technology and photosensitive synthetic subunits, the VLSIPS apparatus allows for the stepwise synthesis of polymers according to a positionally defined matrix pattern. Each oligonucleotide probe will be synthesized at known and defined positional locations on the substrate. This forms a matrix pattern of known relationship between position and specificity of interaction. The VLSIPS technology allows the production of a very large number of different oligonucleotide probes to be simultaneously and automatically synthesized including numbers in excess of about $10^2$, $10^3$, $10^4$, $10^5$, $10^6$, or even more, and at densities of at least about $10^2$, $10^3/cm^2$, $10^4/cm^2$, $10^5/cm^2$ and up to $10^6/cm^2$ or more. This application discloses methods for synthesizing polymers on a silicon or other suitably derivatized substrate, methods and chemistry for synthesizing specific types of biological polymers on those substrates, apparatus for scanning and detecting whether interaction has occurred at specific locations on the substrate, and various other technologies related to the use of a high density very large scale immobilized polymer substrate. At a size of about 30 microns by 30 microns, one million regions would take about 11 centimeters square or a single wafer of about 4 centimeters by 4 centimeters. Thus the present technology provides for making a single matrix of that size having all one million plus possible oligonucleotides. Region size is sufficiently small to correspond to densities of at least about 5 regions/$cm^2$, 20 regions/$cm^2$, 50 regions/$cm^2$, 100 regions/$cm^2$, and greater, including 300 regions/$cm^2$, 1000 regions/$cm^2$, 3K regions/$cm^2$, 10K regions/$cm^2$, 30K regions/$cm^2$, 100K regions/cm², 300K regions/cm² or more, even in excess of one million regions/cm².

A. Overview

The present invention is based, in part, on the ability to perform a step wise series of reactions which either extend or degrade a polymer by defined units.

FIG. 1 schematizes a simplified linear two monomer polymer made up of A type and B type subunits. A degradative scheme is illustrated. Panel A depicts a matrix with two different polymers located at positions 10 and 14, but with no polymer linked at position 12. A reaction is employed to label all of these polymers at the terminus opposite the attachment of the monomer. Panel B illustrates a label (designated by an asterisk) incorporated at position 16 on the terminal monomers. A scan step is performed to locate positions 10 and 14 where polymers have been linked, but no polymer is located at position 12. The entire matrix is exposed to a regent which is specific for removing single terminal A monomers, which are also labeled. The regent is selected to remove only a single monomer; it will not remove further A monomers. Removal of the labeled A monomer leaves a substrate as illustrated in panel C. A scan step is performed, and compared with the previous scan, indicates that the polymer located at position 12 has lost its label, i.e, that polymer at 12 terminated with an A monomer. The entire matrix is then exposed to a second reagent which is specific for removing terminal B monomers which are also labeled. Note that only a single B on each monomer is removed and that successive B monomers are not affected. Removal of the labeled B monomer leaves a substrate as illustrated-in panel D. Another scan step is performed, indicating that the polymer located at position 14 has lost its label, i.e., it terminated with a B monomer. The sequence of treatments and scans is repeated to determine the successive monomers. It will be recognized that if the labeled A and B are distinguishable, i.e., the label on polymers at sites 10 and 14 may be distinguished, a single removal step can be performed to convert the substrate as illustrated in panel B directly to that illustrated in panel D.

An alternative embodiment employs synthetic reactions where a synthetic product is made at the direction of the attached polymer. The method is useful in the synthesis of a complementary nucleic acid strand by elongation of a primer as directed by the attached polymer.

Figure 2:
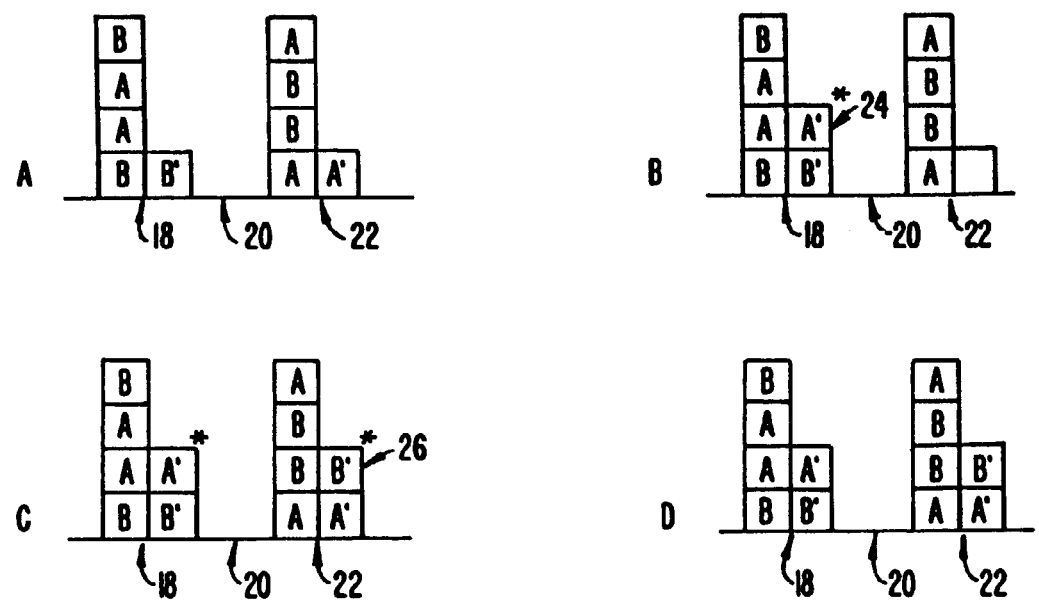
FIG. 2 illustrates a simplified and schematized embodiment of a synthetic scheme for polymer sequencing.

FIG. 2 illustrates a similar simplified polymer scheme, where the A and B monomer provide a complementary correspondence to A' and B' respectively. Thus, an A monomer directs synthetic addition of an A' monomer and a B monomer directs synthetic addition of a B' monomer. Panel A depicts monomers attached at locations 18 and 22, but not at location 20. Each polymer already has one corresponding complementary monomer A'. The matrix, with polymers, is subjected to an elongation reaction which incorporates, e.g., single labeled A' monomers 24 but not B' monomers, as depicted in panel B. The label is indicated by the asterisk. Note that only one A monomer is added. A scan step is performed to determine whether polymers located at positions 18 or 22 have incorporated the labeled A' monomers. The polymer at position 18 has, while the polymer at position 22 has not. Another elongation reaction which incorporates labeled B' monomers 26 is performed resulting in a matrix as depicted in panel C. Again note that only one, and not successive B' monomers, is added. Another scan is performed to determine whether a polymer located at sites 18 or 22 has incorporated a labeled B' monomer, and the result indicates that the polymer located at site 22 has incorporated the labeled B' monomer. A next step removes all of the labels to provide a substrate as depicted in panel D. As before, if the polymer which incorporated a labeled A' monomer is distinguishable from a polymer which incorporated a labeled B' monomer, the separate elongation reactions may be combined producing a panel C type matrix directly from a panel A type matrix and the scan procedure can distinguish which terminal monomer was incorporated.

It will be appreciated that the process may be applied to more complicated polymers having more different types of monomers. Also, the number of scan steps can be minimized if the various possible labeled monomers can be differentiated by the detector system.

Typically, the units will be single monomers, though under certain circumstances the units may comprise dimers, trimers, or longer segments of defined length. In fact, under certain circumstances, the method may be operable in removing or adding different sized units so long as the units are distinguishable. However, it is very important that the reagents used do not remove or add successive monomers. This is achieved in the degradative method by use of highly specific reagents. In the synthetic mode, this is often achieved with removable blocking groups which prevent further elongation.

Figure 3:
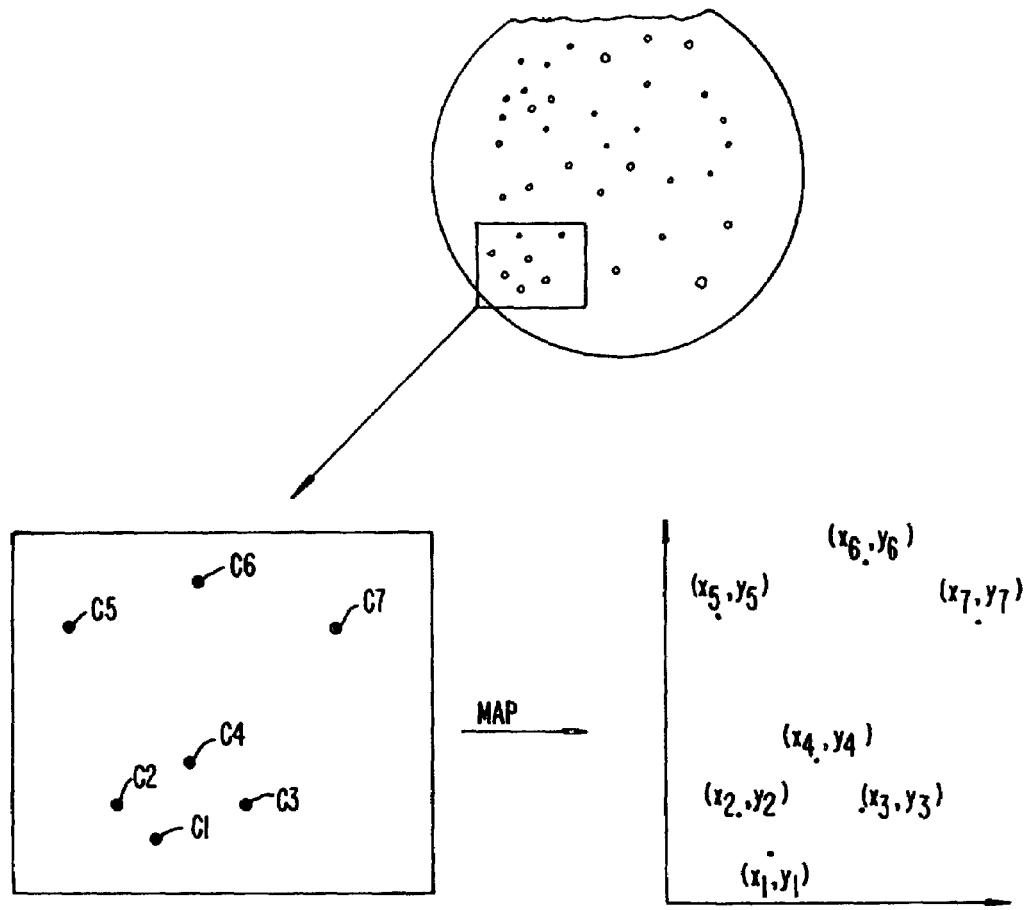
FIG. 3 illustrates a coordinate mapping system of a petri plate containing colonies. Each position of a colony can be assigned a distinct coordinate position.

One important aspect of the invention is the concept of using a substrate having homogeneous clusters of polymers attached at distinct matrix positions. The term "cluster" refers to a localized group of substantially homogeneous polymers which are positionally defined as corresponding to a single sequence. For example, a coordinate system will allow the reproducible identification and correlation of data corresponding to distinct homogeneous clusters of polymer locally attached to a matrix surface. FIG. 3 illustrates a mapping system providing such a correspondence, where transfer of polymers from a producing colony of organisms to a matrix preserves spatial information thereby allowing positional identification. The positional identification allows correlation of data from successive scan steps.

In one embodiment, bacterial colonies producing polymers are spatially separated on the media surface of a petri plate as depicted in panel A. Alternatively, phage plaques on a bacterial lawn can exhibit a similar distribution. A portion of panel A is enlarged and shown in panel B. Individual colonies are labeled C1–C7. The position of each colony can be mapped to positions on a coordinate system, as depicted in panel C. The positions of each colony can then be defined, as in a table shown in panel D, which allows reproducible correlation of scan cycle results.

Although the preferred embodiments are described with respect to a flat matrix, the invention may also be applied using the means for correlating detection results from multiple samples after passage through batch or continuous flow reactions. For example, spatially separated polymers may be held in separate wells on a microtiter plate. The polymers will be attached to a substrate to retain the polymers as the sequencing reagents are applied and removed.

The entire substrate surface, with homogeneous clusters of polymer attached at defined positions, may be subjected to batch reactions so the entire surface is exposed to a uniform and defined sequence of reactions. As a result, each cluster of target polymers for sequencing will be subjected to similar reactive chemistry. By monitoring the results of these reactions on each cluster localized to a defined coordinate position, the sequence of the polymer which is attached at that site will be determined.

Figure 4:
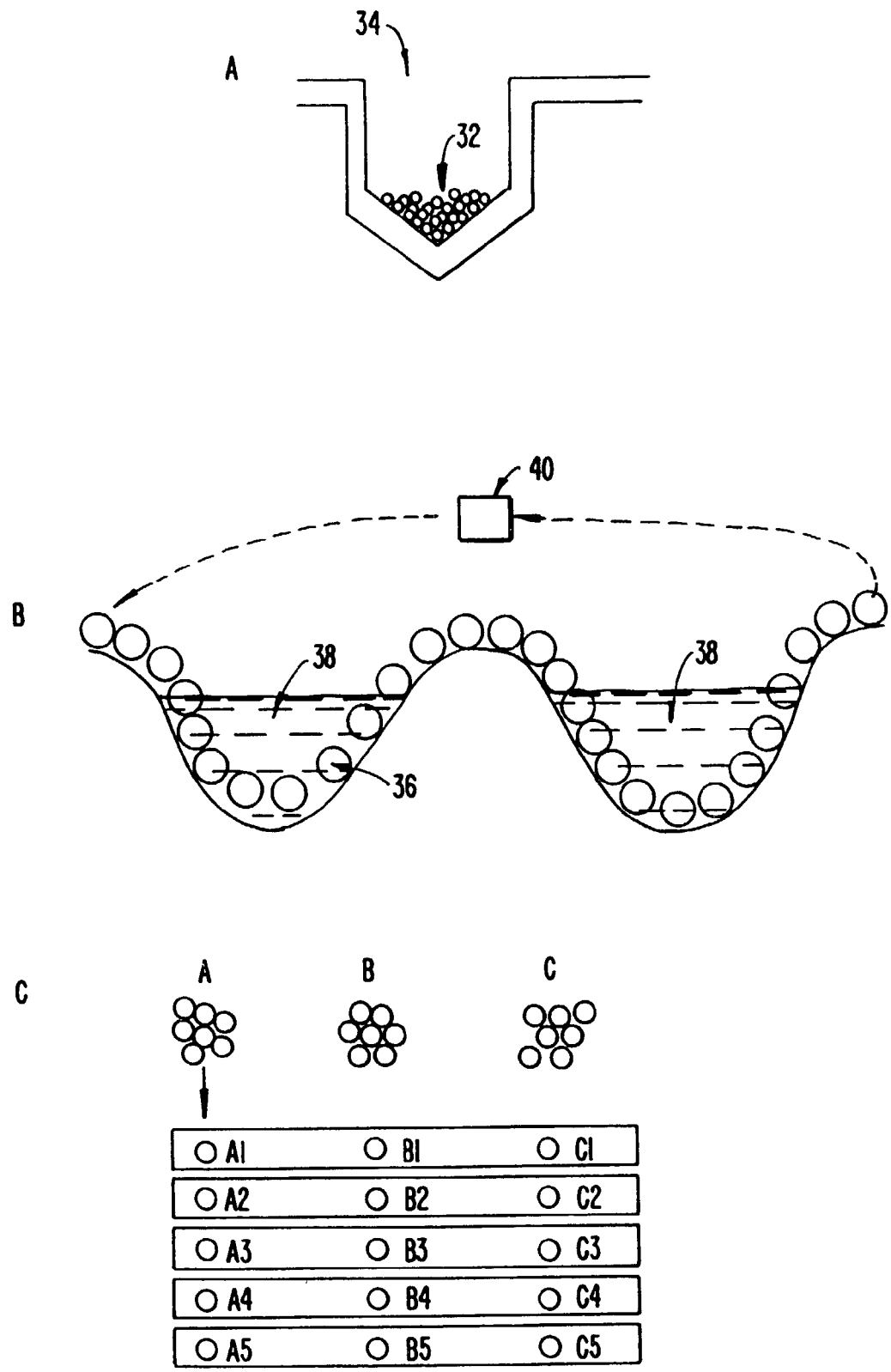
FIG. 4 illustrates various modified embodiments of the substrates.

FIG. 4, panel A illustrates solid phase attached polymers linked to particles 32 which are individually sequestered in separate wells 34 on a microtiter plate. The scanning system will separately scan each well. FIG. 4 panel B illustrates marbles 36 to which polymers are attached. The marbles are automatically fed in a continuous stream through the reaction reagents 38 and past a detector 40. The marbles may be carefully held in tubes or troughs which prevent the order of the beads from being disturbed. In a combination of the two embodiments, each polymer is attached to a plurality of small marbles, and marbles having each polymer are separated, but retained in a known order. Each marble is, in batch with a number of analogous marbles having other polymers linked individually to them, passed through a series of reagents in the sequencing system. For example, A2, B2, and C2 are subjected to sequencing reactions in batch, with label incorporated only for the second monomer A3, B3, and C3, are likewise treated to determine the third monomer. Likewise for $A_n$, $B_n$, and $C_n$. However, within each batch, the detection will usually occur in the order A, B, and C, thereby providing for correlation of successive detection steps for the A polymer beads, for the B polymer beads, and for the C polymer beads.

Figure 5:
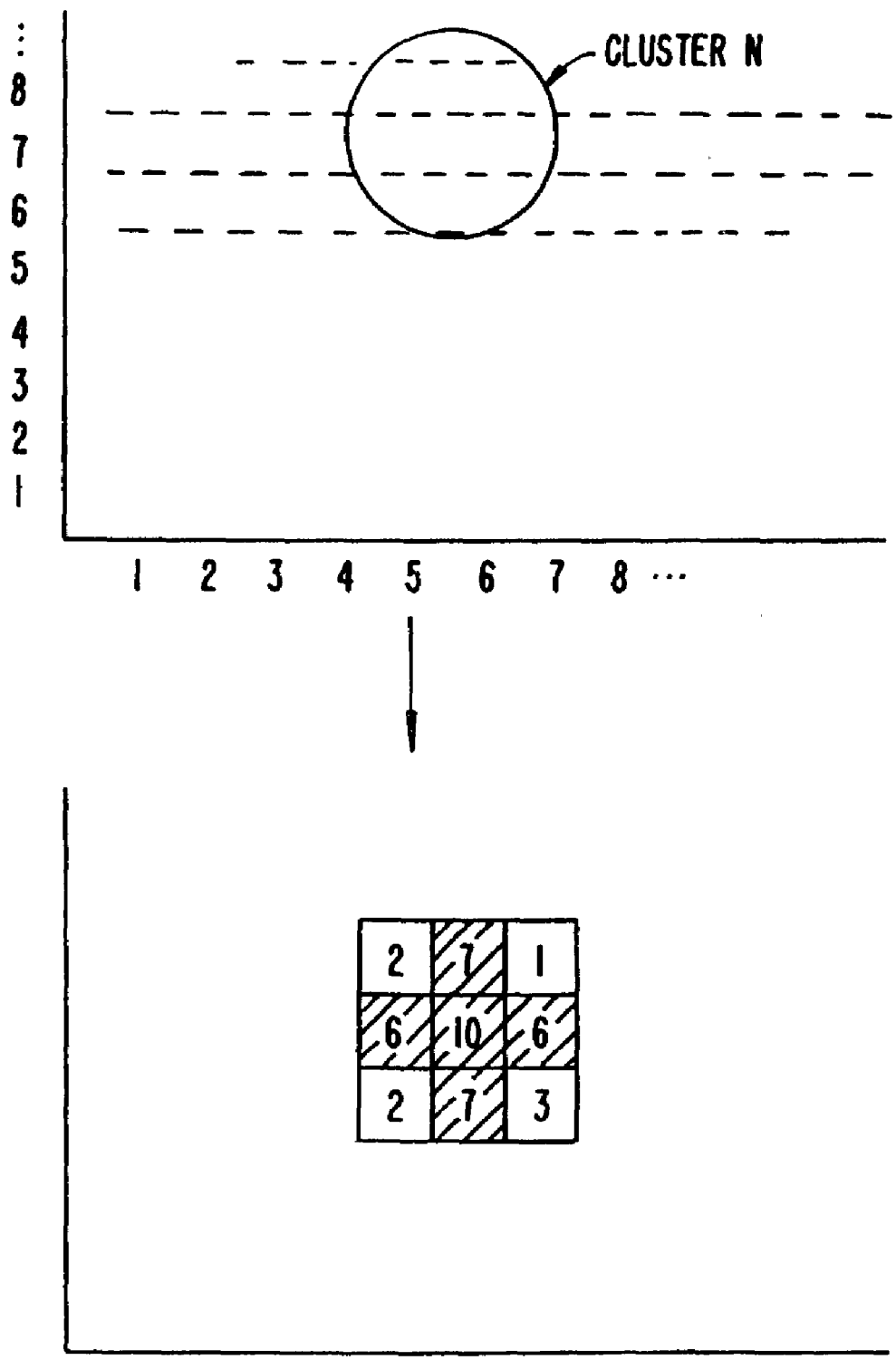
FIG. 5 illustrates an idealized scanning result corresponding to a particular colony position.

FIG. 5 illustrates a signal which might result from a particular defined position. Panel A illustrates the position of a given colony relative to the positions corresponding to the positional map. The scan system will typically determine the amount of signal, or type of signal, at each position of the matrix. The scan system will adjust the relationship of the detector and the substrate to scan the matrix in a controllable fashion. An optical system with mirrors or other elements may allow the relative positions of the substrate and detection to be fixed. The scanner can be programmed to scan the entire substrate surface in a reproducible manner, or to scan only those positions where polymer clusters have been localized. A digital data map, panel B, can be generated from the scan step.

Thus, instead of subjecting each individual and separated polymer to the series of reactions as a homogeneous sample, a whole matrix array of different polymers targeted for sequencing may be exposed to a series of chemical manipulations in a batch format. A large array of hundreds, thousands, or even millions of spatially separated homogeneous regions may be simultaneously treated by defined sequencing chemistry.

The use of a coordinate system which can reproducibly assay a defined position after each reaction cycle can be advantageously applied according to this invention. For example, a colony plaque lift of polymers can be transferred onto a nitrocellulose filter or other substrate. A scanning detector system will be able to reproducibly monitor the results of chemical reactions performed on the target polymers located at the defined locations of particular clones. An accurate positioning can be further ensured by incorporating various alignment marks on the substrate.

The use of a high resolution system for monitoring the results of successive sequencing steps provides the possibility for correlating the scan results of each successive sequencing reaction at each defined position.

The invention is dependent, in part, upon the stepwise synthesis or degradation of the localized polymers as schematized in FIGS. 1 and 2. The synthetic scheme is particularly useful on nucleic acids which can be synthesized from a complementary strand. Otherwise, a stepwise degradation scheme may be the preferred method. Although single monomer cycles of synthesis or degradation will usually be applicable, in certain cases the technology will be workable using larger segments, e.g., dimers or trimers, in the cyclic reactions.

The present invention also provides methods for production or selection of monomer-specific degradative reagents based upon catalytic antibody constructs. Antibody binding sites exhibiting specificity for binding particular terminal monomers can be linked to cleavage reagents or active sites of cleavage enzymes. Thus, reagents which are specific for particular terminal nucleotides may function to remove them in a specific fashion.

The invention also makes use of a means for detecting or labeling the polymers. Particular sequencing chemistry can be selected for specificity in reacting with terminal monomer units. Alternatively, indirect labeling methods may be applied which can distinguish between different terminal monomers. Another alternative scheme allows for terminal labeling which is not monomer-specific, but with the determination of the monomer based upon specificity of post-label reagents or upon monomer-distinguishable labels. Suitable such reagents will be antibodies or other reagents having specificity for distinguishing between different labeled terminal monomer residues and cleaving only those labeled monomer residues.

Thus, although neither the reaction nor the label need necessarily be specific, at least one of the pair must be specific. This ensures that a comparison of label signal before and after a reaction allows determination of the change in label signal after monomer specific reactions are performed, and thereby providing the means to deduce the identity of the monomer at a given position.

B. Substrate/Matrix

The substrate or matrix has relatively few constraints on its composition. Preferably, the matrix will be inert to the sequencing reactions to which the polymers attached thereto will be subjected. Typically, a silicon or glass substrate will be used, but other suitable matrix materials include ceramics, or plastics, e.g., polycarbonate, polystyrene, delrin, and cellulose, and any other matrix which satisfies these functional constraints.

In one embodiment, the matrix should be sufficiently nondeformable that the scanning system can reproducibly scan the matrix and reliably correlate defined positions with earlier and later scan operations. However, by including alignment markings on the substrate, the need for absolute rigidity of the substrate may be reduced.

In an alternative embodiment, the matrix may merely be large enough that the attached polymer may be separated from a liquid phase containing the sequencing reagents. In this embodiment, a single detection unit is used to analyze the label in a multiplicity of different samples after each of the reaction steps. Thus, different samples may be separably treated in distinct wells of a microtiter dish.

Separate homogeneous polymers can be introduced to solid phase beads in each microtiter well. Sequencing reagents may be individually introduced separately into each well, or transferred from well to well with the polymers remaining in the correct well due to their solid phase attachments.

In an alternative approach, the solid phase matrix may be marbles or other particularly shaped articles. Spherical shapes, solid or hollow, are preferred because they can be easily transported through troughs or tubing which retains their relative orders. By feeding a succession of beads through appropriate reaction baths and past a detector in a known and retained order, a succession of label detection results from a bead may be correlated and converted into a polymer sequence.

The attachment of the target homogeneous clusters of target polymers to the substrate can be achieved by appropriate linkage chemistry. As indicated before, the linkage should be stable and insensitive to the sequencing reagents used. The specific linkages will depend, of course, upon the particular combination of substrate and polymer being used.

Typically, the most useful chemical moieties which will be used are amines. Typical substrate derivatized groups include aminopropyl triethoxysilane, hydroxypropylacylate, or hydroxy reagents, see, e.g., U.S. Ser. No. 07/624,120, a divisional of which has issued as U.S. Pat. No. 5,744,101 (automated VLSIPS®). Typical polymer derivatized groups include nitroveratryl and nitroveratryl oxycarbonyl. Linkage types are also illustrated and detailed in U.S. Ser. No. 07/624,120, a divisional of which has issued as U.S. Pat. No. 5,744,101 (automated VLSIPS®), and U.S. Ser. No. 07/624,114, (a grandchild of which has issued as U.S. Pat. No. 5,800,992) (sequencing by hybridization).

Figure 6:
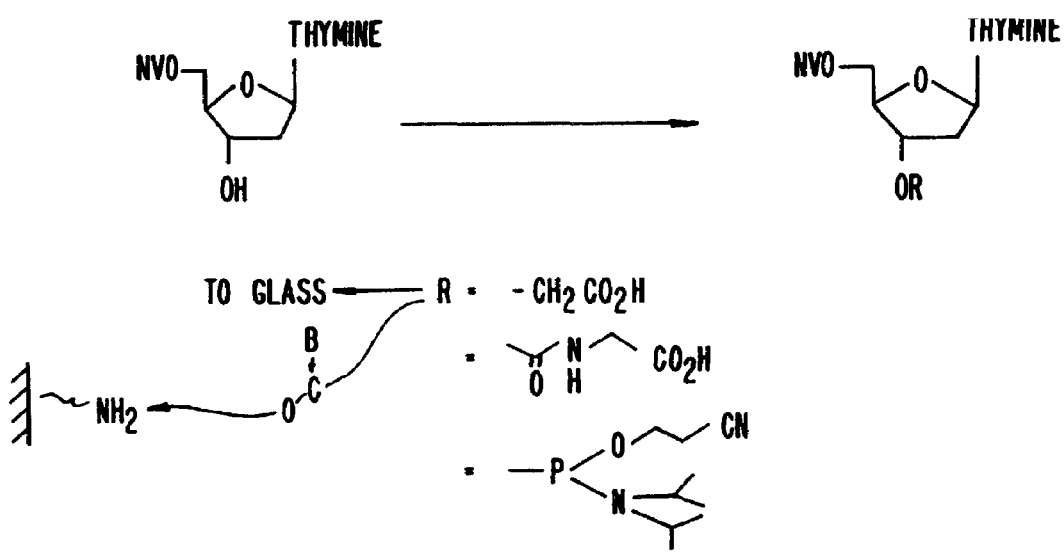
FIG. 6 illustrates particular linkers useful for attaching a nucleic acid to a silicon substrate. Note that thymine may be substituted by adenine, cytidine, guanine, or uracil.

FIG. 6 illustrates one preferred linkage chemistry for nucleic acids. An NVO-derivatized U.S. Ser. No. 07/624,120, a divisional of which has issued as U.S. Pat. No. 5,744,101 (automated VLSIPS®). The specific conditions for synthesis of thymidine are described therein and are adaptable to other nucleotides and nucleosides. The nucleoside analog is further derivatized with an appropriate R group at the 3' hydroxyl. Preferred R groups are indicated in FIG. 6. The linkage produces a photosensitive blocked nucleoside suitable for phosphoramidite synthesis of further polynucleotides which can serve as a complementary strand for hybridization of other polymers. The hybrids of the complementary strands may be covalently crosslinked using acridine dyes or other intercalative reagents, e.g., psoralen. See, e.g., Kornberg (1980) *DNA Replication* Freeman, San Francisco; Wiesehahn, et al. (1978) *Proc. Natl. Acad. Sci. USA* 75:2703–2707, and Sheldon (1986) U.S. Pat. No. 4,582,789 which are each incorporated herein by reference.

The linkage should be substantially inert to the cyclic sequencing reactions and scan cycles. Usually, the linkage will be at a defined and homogeneous polymer position, preferably at the end opposite where the sequencing chemistry takes place. Although the type of linkage is dependent upon the polymer being sequenced, various types of polymers have preferred linkages. For polypeptides, amino terminal or carboxyl terminal linkages will be preferred. Specific amino terminal linkages include amino butyric acid, amino caproic acids, and similar carboxylic acids. Specific carboxyl terminal linkages include butyric acid, caproic acid, and other carboxylic acids, hydrocarbon, and ethers. See U.S. Ser. No. 07/435,316 (VLSIPS® parent), and U.S. Ser. No. 07/492,462 (VLSIP® CIP) (now U.S. Pat. No. 5,143,854), which are incorporated herein by reference. For nucleic acids, the linkages will typically be either 5' or 3' linkages. Suitable 3' linkages include those illustrated in FIG. 6, and others described in U.S. Ser. No. 07/624,114, (a grandchild of which has issued as U.S. Pat. No. 5,800,992) (sequencing by hybridization).

Alternatively, for complementary polymers, particularly nucleic acids, linkage may be via crosslinkage of the complementary polymers where the complementary stand is directly attached to the matrix. Acridine dyes, e.g., psoralen, or a similar crosslinking agent between the strands can be used. See, e.g., Dattagupta, et al., "Coupling of Nucleic Acids to Solid Support By Photochemical Methods," U.S. Pat. No. 4,713,326; and U.S. Pat. No. 4,542,102; and Chattejee, M. et al. (1990) *J. Am. Chem. Soc.* 112:6397; which describe useful crosslinking reagents, and are hereby incorporated herein by reference.

For polynucleotides, the preferred attachment to the matrix is through a synthetic oligomer by the 5' end of each target sequence. This oligomer is designed to anneal to the desired target templates used in a synthetic system or to the polynucleotide used in the degradation approach. In one embodiment, a vector sequence which is complementary to the immobilized oligonucleotide is incorporated adjacent the cloning inserts, thereby providing a common complementary sequence for each insert. In particular, a cloning vector will be selected with a defined sequence adjacent the insert. See, e.g., Sambrook et al., (1989) *Molecular Cloning: A Laboratory Manual*, Vols. 1–3, Cold Spring Harbor Press, which is hereby incorporated herein by reference. This defined sequence is used, in some embodiments, as a common linker for all of the vector inserts. The inserts, adjacent to this linker, will be transferable by hybridization to the matrix linked complementary sequences. The hybrids are crosslinked by addition of a suitable crosslinker under appropriate conditions, for example, photocrosslinking by psoralen with uv light. See, e.g., Song et al. (1979) *Photochem. Photobiol.* 29:1177–1197; Cimino et al. (1985) *Ann. Rev. Biochem.* 54:1151–1193; and Parsons (1980) *Photochem. Photobiol.* 32:813–821; each of which is incorporated herein by reference. Using these approaches, the oligonucleotide linker serves as both the attachment linker and the polymerization primer.

FIG. 6 illustrates a preferred 3' terminal linkage designed for a phosphoramidite linkage of a synthetic primer and the reactions forming them. The chemical reactions for actually performing the linkage will be similar to those used for oligonucleotide synthesis instruments using phosphoramidite or similar chemistry. Applied Biosystems, Foster City, Calif. supplies oligonucleotide synthesizers.

C. Scanning System

The scanning system should be able to reproducibly scan the substrate. Where appropriate, e.g., for a two dimensional substrate where the polymers are localized to positions thereon, the scanning system should positionally define the clusters attached thereon to a reproducible coordinate system. It is important that the positional identification of clusters be repeatable in successive scan steps. Functionally, the system should be able to define physical positions to a coordinate system as described above and illustrated in FIGS. 3 and 4.

In alternative embodiments, the system can operate on a cruder level by separately detecting separate wells on a microtiter plate, or by scanning marbles which pass by the detector in an embodiment as described above and illustrated in FIG. 4.

The scanning system would be similar to those used in electrooptical scanning devices. See, e.g., the fluorescent detection device described in U.S. Ser. No. 07/492,462 (VLSIP® CIP), now U.S. Pat. No. 5,143,854, and U.S. Ser. No. 07/624,120, a divisional of which has issued as U.S. Pat. No. 5,744,101 (automated VLSIPS®). The system could exhibit many of the features of photographic scanners, digitizers or even compact disk reading devices. For example, a model no. PM500-A1 x-y translation table manufactured by Newport Corporation can be attached to a detector unit. The x-y translation table is connected to and controlled by an appropriately programmed digital computer such as an IBM PC/AT or AT compatible computer. The detection system can be a model no. R943-02 photomultiplier tube manufactured by Hamamatsu, attached to a preamplifier, e.g., a model no. SR440 manufactured by Stanford Research Systems, and to a photon counter, e.g., an SR430 manufactured by Stanford Research System, or a multichannel detection device. Although a digital signal may usually be preferred, there may be circumstances where analog signals would be advantageous.

The stability and reproducibility of the positional localization in scanning will determine, to a large extent, the resolution for separating closely positioned polymer clusters in a 2 dimensional substrate embodiment. Since the successive monitoring at a given position depends upon the ability to map the results of a reaction cycle to its effect on a positionally mapped cluster of polymers, high resolution scanning is preferred. As the resolution increases, the upper limit to the number of possible polymers which may be sequenced on a single matrix will also increase. Crude scanning systems may resolve only on the order of 1000μ, refined scanning systems may resolve on the order of 100μ, more refined systems may resolve on the order of about 10μ with optical magnification systems a resolution on the order of 1.0μ is available, and more preferably a resolution on the order of better than 0.01μ is desired. The limitations on the resolution may be diffrication limited and advantages may arise from using shorter wavelength radiation for the photo-optical deprotection fluorescent scanning steps. However, with increased resolution, the time required to fully scan a matrix will be increased and a compromise between speed and resolution will necessarily be selected. Parallel detection devices which will provide high resolution with shorter scan times will be applicable where multiple detectors will be moved in parallel.

With other embodiments, resolution often is not so important and sensitivity might be emphasized. However, the reliability of a signal may be pre-selected by counting photons and continuing to count for a longer period at positions where intensity of signal is lower. Although this will decrease scan speed, it can increase reliability of the signal determination. Various signal detection and processing algorithms may be incorporated into the detection system, such as described in U.S. Ser. No. 07/624,120, a divisional of which has issued as U.S. Pat. No. 5,744,101 (activated VLSIPS). In one embodiment, the distribution of signal intensities of pixels across the region of signal are evaluated to determine whether the distribution of intensities corresponds to a time positive signal.

The detection system for the signal or label will depend upon the label used, which may be defined by the chemistry available. For optical signals, a combination of an optical fiber or charged couple device (CCD) may be used in the detection step. In those circumstances where the matrix is itself transparent to the radiation used, it is possible to have an incident light beam pass through the substrate with the detector located opposite the substrate from the polymers. For electromagnetic labels, various forms of spectroscopy systems can be used. Various physical orientations for the detection system are available and discussion of important design parameters is provided, e.g., in Jovin, Adv. in Biochem. Bioplyms, which is hereby incorporated herein by reference.

Various labels which are easily detected include radioactive labels, heavy metals, optically detectable labels, spectroscopic labels and the like. Various photoluminescent labels include those described in U.S. Ser. No. 07/624,114, a grandchild of which has issued as U.S. Pat. No. 5,800,992 (sequencing by hybridization). Protection and deprotection are described, e.g., in McCray, et al. (1989) *Ann. Rev. Biophysical Chemistry* 18:239–270, and U.S. Ser. No. 07/624,120, a divisional of which has issued as U.S. Pat. No. 5,744,101 (automated VLSIP®), each of which is hereby incorporated herein by reference.

With a processing system, the speed of scanning may be dramatically increased with a system which only scans positions where known clusters of polymer are attached. This allows the scanning mechanism to skip over areas which have been determined to lack any polymer clusters and avoids loss of time in scanning useless regions of the matrix. Moreover, various problems with spurious or overlapping signals may be adjusted for by appropriate analysis.

Figure 7:
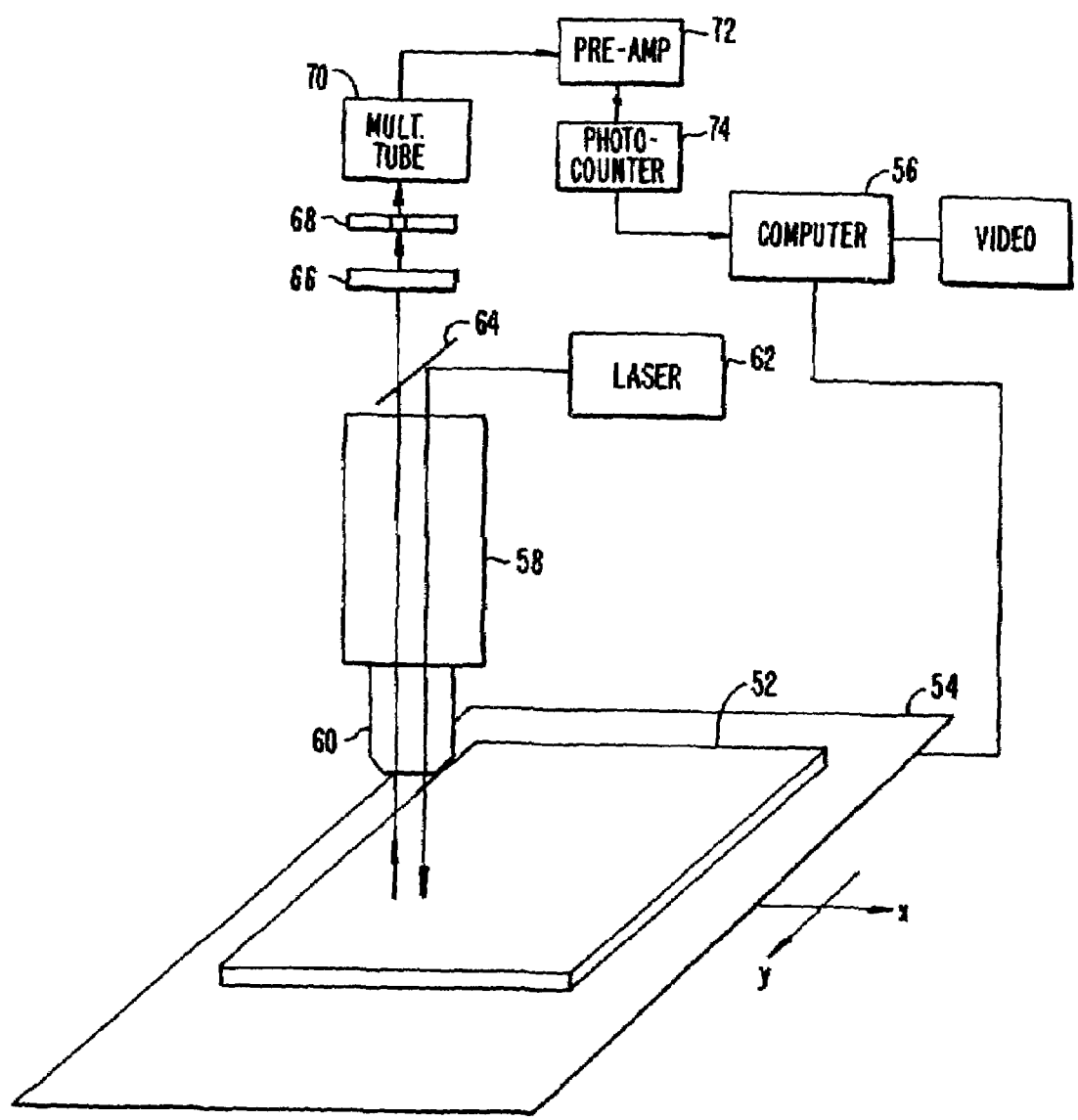
FIG. 7 illustrates an embodiment of the scanning system and reaction chamber.

A scanning apparatus which may be used for the presently described uses is schematically illustrated in FIG. 7. A substrate 52 is placed on an x-y translation table 54. In a preferred embodiment the x-y translation table is a model no. PM500-A1 manufactured by Newport Corporation. The x-y translation table is connected to and controlled by an appropriately programmed digital computer 56 which may be, for example, an appropriately programmed IBM PC/AT or AT compatible computer. Of course, other computer systems, special purpose hardware, or the like could readily be substituted for the AT computer used herein for illustration. Computer software for the translation and data collection functions described herein can be provided based on commercially available software including, for example, "Lab Windows" licensed by National Instruments, which is incorporated herein by reference for all purposes.

The substrate and x-y translation table are placed under a microscope 58 which includes one or more objectives 60. Light (about 488 nm) from a laser 62, which in some embodiments is a model no. 2020-05 argon ion laser manufactured by Spectraphysics, is directed at the substrate by a dichroic mirror 64 which passes greater than about 520 nm wavelength light but reflects 488 nm light. Dichroic mirror 64 may be, for example, a model no. FT510 manufactured by Carl Zeiss. Light reflected from the mirror then enters the microscope 58 which may be, for example, a model no. Axioscop 20 manufactured by Carl Zeiss. Fluorescein-marked materials on the substrate will fluoresce >488 nm light, and the fluoresced light will be collected by the microscope and passed through the mirror. The fluorescent light from the substrate is then directed through a wavelength filter 66 and, thereafter through an aperture plate 68. Wavelength filter 66 may be, for example, a model no. OG530 manufactured by Melles Griot and aperture plate 68 may be, for example, a model no. 477352/477380 manufactured by Carl Zeiss.

The fluoresced light then enters a photomultiplier tube 70 which in one embodiment is a model no. R943-02 manufactured by Hamamatsu, the signal is amplified in preamplifier 72 and photons are counted by photon counter 74. The number of photons is recorded as a function of the location in the computer 56. Pre-Amp 72 may be, for example, a model no. SR440 manufactured by Stanford Research Systems and photon counter 74 may be a model no. SR430 manufactured by Stanford Research Systems. The substrate is then moved to a subsequent location and the process is repeated. In preferred embodiments the data are acquired every 1 to 100 μm with a data collection diameter of about 0.8 to 10 μm preferred. In embodiments with sufficiently high fluorescence, a CCD detector with broadfield illumination is utilized.

By counting the number of photons generated in a given area in response to the laser, it is possible to determine where fluorescent marked molecules are located on the substrate. Consequently, for a substrate which has a matrix of polypeptides, for example, synthesized on the surface thereof, it is possible to determine which of the polypeptides has incorporated a fluorescently marked monomer.

According to preferred embodiments, the intensity and duration of the light applied to the substrate is controlled by varying the laser power and scan stage rate for improved signal-to-noise ratio by maximizing fluorescence emission and minimizing background noise. Signal analysis may improve the resolution and reliability of the system. The time of photon counting may be varied at various positions to provide high signal to background or noise.

D. Synthetic or Degradative Cycle

The present invention provides a substrate with positionally separated polymers for sequencing. The separation may be by solid phase carriers separated in separate wells, by separately manipulable carriers such as beads or marbles, or by physical separation of regions on a two-dimensional substrate surface. Each cluster region is a target for the sequencing reactions. Although the reactions are, in various embodiments, performed on all the clusters together, each cluster can be individually analyzed by following the results from the sequence of reactions on polymer clusters at positionally defined locations.

Figure 8:
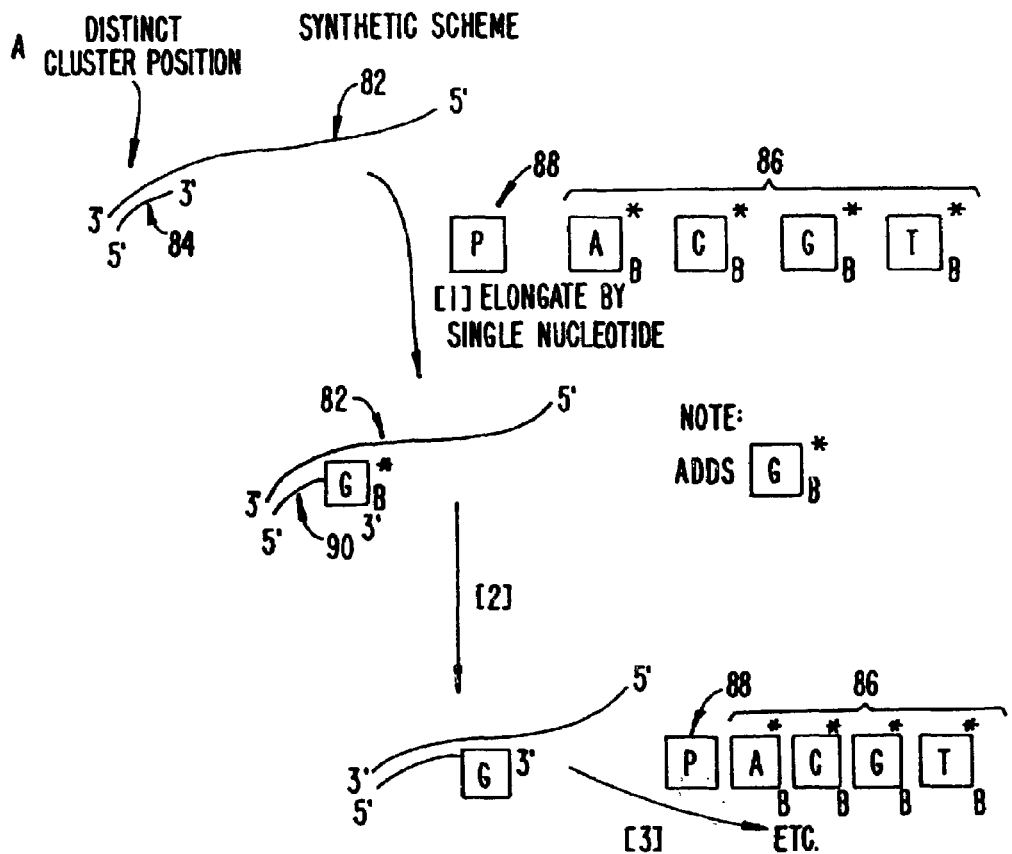
FIG. 8 illustrates the application of the synthetic scheme for sequencing as applied to a nucleic acid cluster localized to a discrete identified position.
Figure 8:
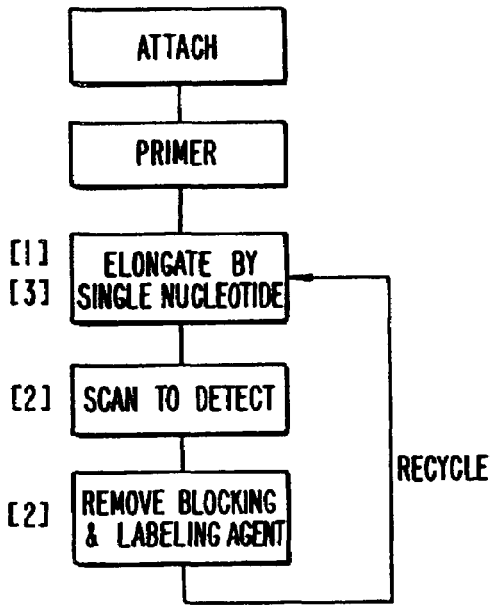

The synthetic mode, as illustrated in FIG. 1 is easily applied to the sequencing of nucleic acids, since one target strand may serve as the template to synthesize the complementary strand. The nucleic acid can be DNA, RNA or mixed polymers. For the purposes of illustration, and not by limitation, the sequencing steps for DNA are described in detail. The synthetic mode, an example of which is depicted in FIG. 8 for nucleotides, may also be useful in circumstances where synthesis occurs in response to a known polymer sequence. The synthetic scheme depends, in part, on the stepwise elongation by small and identifiable units. A polymerase is used to extend a primer complementary to a target template. The primer is elongated one nucleotide at a time by use of a particular modified nucleotide analog to which a blocking agent is added and which prevents further elongation. This blocking agent is analogous to the dideoxy nucleotides used in the Sanger and Coulson sequencing procedure, but in certain embodiments here, the blockage is reversible. This analog is also labeled with a removable moiety, e.g., a fluorescent label, so that the scanning system can detect the particular nucleotide incorporated after its addition to the polymerization primer.

Panel 4A illustrates the cycle of sequence reactions in one embodiment. The template polymer 82 located at a particular site has already been linked to substrate. The template 82 and complementary primer 84 are hybridized. Often, the primer 84 is common to all of the target template sequences, selected by its common occurrence on a selected cloning vector. The primer 84 is also often covalently crosslinked to the target template 82 using psoralen and U.V. light.

Labeled and blocked monomers 86 are shown, the label depicted by the asterisk and the polymerization blocking groups indicated by B. A compatible polymerase 88 which can elongate the primer with the labeled blocked monomers 86 is used in reaction 1. In the preferred embodiment, the separate labeled monomers can be distinguished from one another by the wavelength of fluorescent emission.

In the example illustrated, a labeled blocked guanosine monomer has been incorporated into the elongated primer 90.

Step 2 is a scan, where the signal at the position corresponding to template 82 indicates that the guanosine analog was incorporated. Reaction 2 is performed, a removal of both the label and blocking group. It will be recognized that the blocking group prevents elongation by any more than a single nucleotide in each reaction cycle. Reaction 3 is equivalent to reaction 1, though the substrate primer has been elongated by one monomer.

Panel B illustrates the scheme in a logic flow chart. The template 82 is attached to the substrate, either directly or through the primer. Reaction 1 elongates the primer by a single labeled blocked nucleotide. A scan step is performed and the blocking and labeling agents are removed. The elongation reaction is performed and the cycle repeated.

For a nucleic acid, a unit for addition would typically be a single nucleotide. Under certain circumstances, dimers or trimers or larger segments may be utilized, but a larger number of different possible nucleotide elements requires high distinguishability in other steps. For example, there are only four different nucleotide monomer possibilities, but there are sixteen different dimer possibilities. The distinction among four possibilities is more precise and simple than among sixteen dimer possibilities. To prevent elongation by a unit length greater than one monomer, the nucleotide should be blocked at the position of 3' elongation. Usually, the nucleotide will be blocked at the 3' hydroxyl group where successive nucleotides would be attached. In contrast to a dideoxy nucleotide, typically the blocking agent will be a reversible blocking agent thereby allowing for deblocking and subsequent elongation.

Variations may be easily incorporated into the procedure. If the labels on the monomers are not distinguishable, successive substrate scans can be performed after each monomer is provided conditions allowing its incorporation. Alternatively, a small fraction of permanently blocked but reversibly labeled monomers may be incorporated. Those specific molecules which incorporate the blocked monomers are permanently removed from further polymerization, but such is acceptable if the labeling moiety is also removed.

1. Other Monomers one important functional property of the monomers is that the label be removable. The removal reaction will preferably be achieved using mild conditions. Blocking groups sensitive to mild acidic conditions, mild basic conditions, or light are preferred. The label position may be anywhere on the molecule compatible with appropriate polymerization, i.e., complementary to the template, by the selected polymerase. A single polymerase for all of the modified nucleotide is preferred, but a different polymerase for each of the different monomers can be used.

Nucleotide analogs used as chain-terminating reagents will typically have both a labeling moiety and a blocking agent while remaining compatible with the elongation enzymology. As the blocking agent will usually be on the 3' hydroxyl position of the sugar on a nucleotide, it would be most convenient to incorporate the label and the blocking agent at the same site, providing for a single reaction for simultaneous removal of the label and blocking agent. However, it is also possible to put a label on another portion of the nucleotide analog than the 3' hydroxyl position of the sugar, thereby requiring a two-step reaction cycle for removing the blocking and labeling groups.

Analogs will be found by selecting for suitable combinations of appropriate nucleotides with compatible polymerases. In particular, it is desired that a selected polymerase be capable of incorporating a nucleotide, with selectivity, having both the blocking moiety and the label moiety attached. It has been observed that RNA polymerases are less fastidious with respect to the nucleotide analogues which will be polymerized into a growing chain. See, e.g., Rozovaskaya, T., et al. (1977) *Molekulyarnaya Biologiya*, 11:598–610; Kutateladze, T., et al. (1986) *Molekulyarnya Biologiya*, 20:267–276; and Chidgeavadze, Z., et al. (1985)

FEBS Letters, 183:275–278. Moreover, those references also indicate that rather significant chemical moieties may be attached at the 2' or 3' positions on a nucleotide, and still be correctly incorporated at the growing chain terminus.

In particular, it is not necessary that the same nucleotide have both the reversible blocking moiety and the removable labeling moiety, as a combination of two separate nucleotide analogues could be utilized, e.g., N1, which is reversibly blocked and not labeled, and N2, which is irreversibly blocked but removably labeled. Note that the removal of label may be affected by destruction of the label, e.g., fluorescence destruction, or preferably by removal. Both of these nucleotides might be, for instance, A analogues. With the mixture, at an appropriate sequence position of a target sequence, an N1 and N2 nucleotides can be incorporated at an appropriate ratio, and these can be polymerized by either two separate polymerases, or preferably a single polymerase.

For example, two separate polymerases might be necessary, P1 which incorporates N1, and P2 which incorporates N2. At the given location in the sequence, some of the growing polymers will incorporate N1 with P1 polymerase, and others will incorporate N2 with the P2 polymerase. The proportions of N1, N2, P1, and P2 may be titrated to get the desired fractional proportions of the N1 reversibly blocked nucleotides and the N2 labeled but irreversibly blocked nucleotides.

As all of the growing chains have blocked nucleotides, no elongation takes place beyond a single nucleotide. The N2 nucleotides provide a specific label, detected in the scanning step. After determination of the incorporated label, the label may be removed or destroyed, and those irreversibly terminated growing chains become permanently removed from further participation in the sequencing process. Photodestruction may be achieved by a high intensity laser beam of the correct wavelength. See, e.g., March (1977) *Advanced Organic Chemistry: Reactions, Mechanisms and Structure* (2d Ed) McGraw; and Carey and Sundberg (1980) *Advanced Organic Chemistry: part A Structure and Mechanisms*, Plenum.

Next, the reversible blocking moiety is removed, providing a new set of slightly longer polymers ready for the next step. Of course, the amount of label necessary to be incorporated must be detectable, preferably with a clear, unambiguous positive signal. The amount of label incorporated will depend, in part, upon the conditions in the polymizing step and the relative incorporation of the N1 and N2 nucleotides. The proportions of the nucleotides, polymerases, and other reagents may be adjusted to appropriately incorporate the desired proportions of the nucleotides.

In an embodiment where a single polymerase will incorporate both N1 and N2, the relative proportions and conditions to get the correct incorporation levels of the two nucleotides can be titrated. In an alternative preferred embodiment, a single nucleotide will have both the removable label and the reversible blocking moiety.

A similar approach may be necessary where only some fraction of the nucleotide analogues is labeled. Separate polymerases might also be useful for such situations, and each polymerase may have special conditions necessary for activity.

Procedures for selecting suitable nucleotide and polymerase combinations will be readily adapted rom Ruth et al. (1981) *Molecular Pharmacology* 20:415–422; Kutateladze, T., et al. (984) *Nuc. Acids Res.*, 12:1671–1686; Kutateladze, T., et al. (1986) *Molekulyarnaya Biologiya* 20:267–276; Chidgeavadze, Z., et al. (1985) *FEBS Letters*, 183:275–278; and Rozovskaya, T., et al. (1977) *Molekulyarnaya Biologiya* 11:598–610.

The determination of termination activity is done in two steps. First, nucleotide analogues are screened for the ability of the compound to inhibit polymerase activity. Then the nucleotide analogue is tested for base-specific termination as manifested by generating a correct DNA sequencing ladder on a template of known sequence. The appropriate reaction conditions are those used for conventional sequencing reactions with the respective polymerases. The conditions are then modified in the usual ways to obtain the optimal conditions for the particular terminator compound (e.g. concentration of terminator, ratio of terminator to dNTP, Mgtt, and other reagents critical to proper polymerase function.

By way of example, an approach employing the polymerase known as reverse transcriptase (AMV) will be described. The initial conditions are essentially as described by Prober, et al. (1987) *Science* 238: 336–341.

A nucleotide analogue is first selected from the group available from a commercial source such as Amersham, New England Nuclear, or Sigma Chemical Company. In particular, nucleotides which are reversibly blocked from further elongation, especially at the 5' or 3' —OH will be used.

General properties which are desired have been described. Each of these analogs can be tested for compatibility with a particular polymerase by testing whether such polymerase is capable of incorporating the labeled analog. Various polymerases may be screened, either natural forms of the mentioned types, or variants thereof. Polymerases useful in connection with the invention include *E. Coli* DNA polymerase (Klenow fragment); and Klenow and Henningsen (1970) *Proc. Nat'l Acad Sci USA* 65:168–175; and Jacobsen et al. (1974) Eur. J. Biochem. 45:623–627; modified and cloned versions of T7 DNA polymerase (Sequenase™ and Sequenase 2.0™); see Tabor and Richardson (1987) *Proc. Nat'l Acad. Sci. USA* 84:4767–4771; and Tabor and Richardson (1987) *J. Biol. Chem.* 262:15330–15333; Taq DNA polymerase from thermostable Thermus aquaticus; see Chien et at. (1976) *J. Bacterol.* 127:1550–1557; and its cloned version Amplitaq™; Saiki and Gelfand (1989) Amplifications 1:4–6; T4 DNA polymerase; see Nossal (1974) *J. Biol. Chem.* 249:5668–5676, and various reverse transcriptases, both RNA- and DNA-dependent DNA polymerases, e.g., avian retroviruses; see Houts (1979) *J. Virology* 29:517–522; and murine retroviruses; see Kotewicz et al. (1985) *Gene* 35:249–258; Gerard et al. (1986) *DNA* 5:271–279 and Bst polymerase; see Ye, S. and Hong (1987) *Scientia Sinica* 30:503–506.

In order to ensure that only a single nucleotide is added at a time, a blocking agent is usually incorporated onto the 3' hydroxyl group of the nucleotide. Optimally, the blocking agent should be removable under mild conditions (e.g., photosensitive, weak acid labile, or weak base labile groups), thereby allowing for further elongation of the primer strand with a next synthetic cycle. If the blocking agent also contains the fluorescent label, the dual blocking and labeling functions will be achieved without the need for separate reactions for the separate moieties.

The blocking group should have the functional properties of blocking further elongation of the polymer. Additional desired properties are reversibility and inertness to the sequencing reactions. Preferably, where an enzymatic elongation step is used, the monomers should be compatible with the selected polymerase. Specific examples for blocking groups for the nucleic acids include acid or base labile groups at the 3'OH position. See, e.g., Gait (1984) *Oligonucleotide Synthesis: A Practical Approach,* IRL Press, Oxford.

A DNA-dependent DNA polymerase is the polymerases of choice. Polymerases used for conventional DNA sequencing, for example, Klenow fragment of *E. coli* DNA Pol, Sequenase (modified T7 DNA polymerase), Taq (*Thermus aquaticus*) DNA polymerase, Bst (*Bacillus stearothermophilus*), DNA polymerase, reverse transcriptase (from AMV, MMLV, RSV, etc.) or other DNA polymerases will be the polymerases of choice. However, there is a functional constraint that the polymerase be compatible with the monomer analogues selected. Screening will be performed to determine appropriate polymerase and monomer analog combinations.

Removal of the blocking groups may also be unnecessary if the labels are removable. In this approach, the chains incorporating the blocked monomers are permanently terminated and will no longer participate in the elongation processes. So long as these blocked monomers are also removed from the labeling process, a small percentage of permanent loss in each cycle can also be tolerated.

The fluorescent label may be selected from any of a number of different moieties. The preferred moiety will be a fluorescent group for which detection is quite sensitive. Various different fluorescence-labeling techniques are described, for example, in Cambara et al. (1988) "Optimization of Parameters in a DNA Sequenator Using Fluorescence Detection," *Bio/Technol.* 6:816–821; Smith et al. (1985) *Nucl. Acids Res.* 13:2399–2412; and Smith et al. (1986) *Nature* 321:674–679, each of which is hereby incorporated herein by reference. Fluorescent labels exhibiting particularly high coefficients of destruction may also be useful in destroying nonspecific background signals.

Appropriate blocking agents include, among others, light sensitive groups such as 6-nitoveratryl-oxycarbonyl (NVOC), 2-nitobenzyloxycarbonyl (NBOC), α,α-dimethyl-dimethoxybenzyloxycarbonyl (DDZ), 5-bromo-7-nitroindolinyl, o-hydroxy-2-methyl cinnamoyl, 2-oxymethylene anthraquinone, and t-butyl oxycarbonyl (TBOC). Other blocking reagents are discussed, e.g., in U.S. Ser. No. 07/492,462; Patchornik (1970) *J. Amer. Chem. Soc.* 92:6333; and Amit et al. (1974) *J. Org. Chem.* 39:192, all of which are hereby incorporated herein by reference. Additional blocking agents attached to particular positions may be selected according to the functional directives provided herein.

Figure 9:
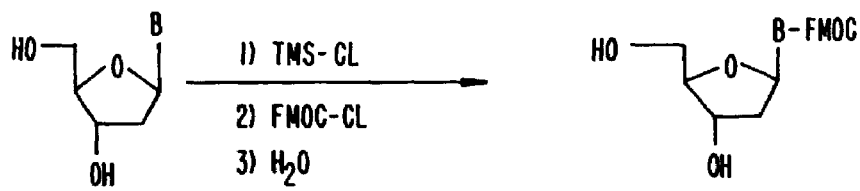
FIG. 9 illustrates the synthesis of a representative nucleotide analog useful in the synthetic scheme. Note that the FMOC may be attached to adenine, cystosine, or guanine.
Figure 9:
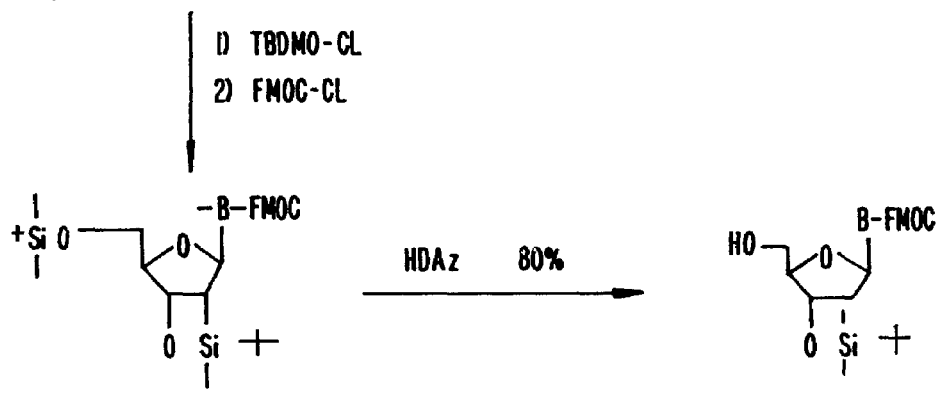
Figure 9:
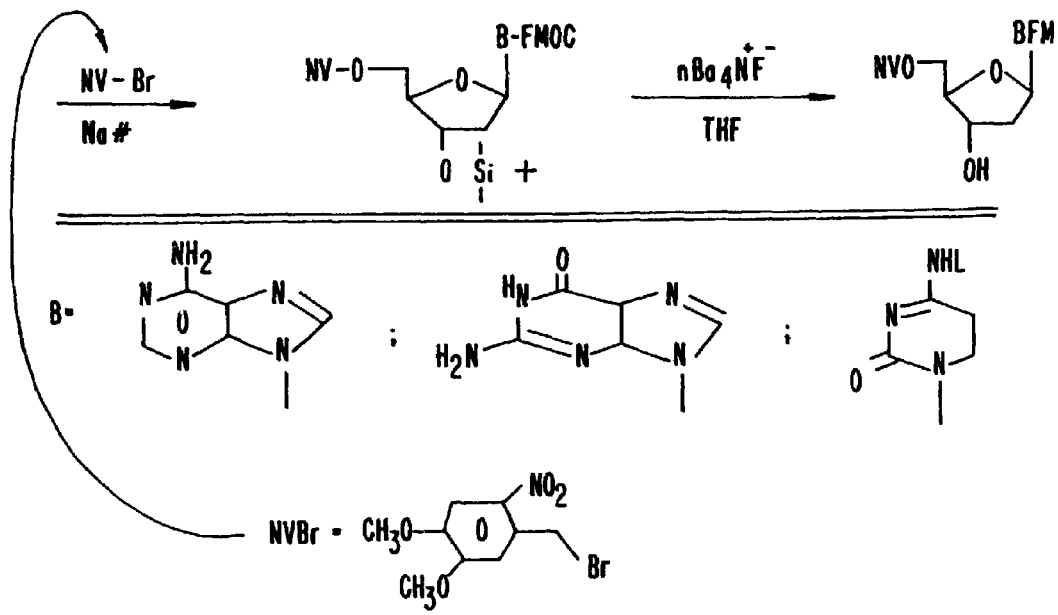

FIG. 9 schematically illustrates the synthesis of a generic protected nucleotide. A suitable nucleotide is labeled with the FMOC fluorescently detectable label by reaction under the conditions described, e.g., in U.S. Ser. No. 07/624,114, (a grandchild of which has issued as U.S. Pat. No. 5,800,992) (sequencing by hybridization), with (TMS-Cl), FMOC-Cl, and $H_2O$. A protection moiety will be added using conditions also described there.

Various nucleotides possessing features useful in the described method can be readily synthesized. Labeling moieties are attached at appropriate sites on the nucleotide using chemistry and conditions as described, e.g., in Gait (1984) *Oligonucleotide Synthesis.* Blocking groups will also be added using conditions as described, e.g., in U.S. Ser. No. 07/624,114, (a grandchild of which has issued as U.S. Pat. No. 5,800,992) (sequencing by hybridization). FIG. 9 also outlines various reactions which lead to useful nucleotides.

Additionally, the selected polymerases used in elongation reactions should be compatible with nucleotide analogs intended for polymerization to the primer. Simple screening procedures for nucleotide and polymerase combinations may be devised to verify that a particular combination is functional. A test using primer with template which directs the addition of the nucleotide analog to be incorporated will determine whether the combination is workable. Natural polymerases or variants thereof may be used under particular defined conditions.

Figure 10:
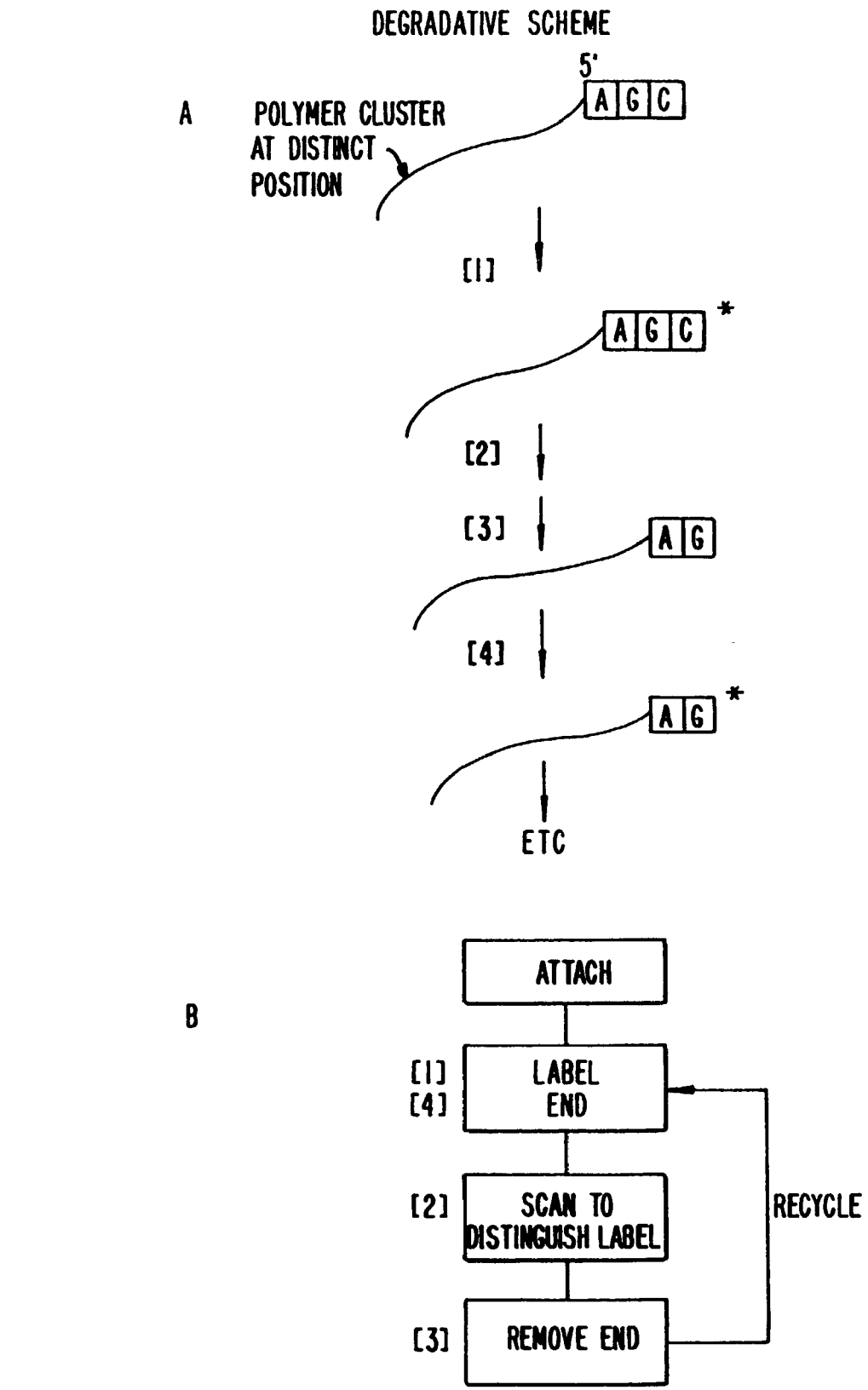
FIG. 10 illustrates the application of the degradative scheme for sequencing as applied to a nucleic acid cluster localized to a discrete identified position.

The degradative scheme is generally illustrated in FIG. 1, an example more generally applicable to biological macromolecular polymers is depicted in FIG. 10. This method is useful for a wider variety of polymers without the limitations imposed by the need to replicate the polymer. The degradative sequencing technique depends, in part, upon the ability to specifically label or distinguish between various different terminal monomers at particular matrix positions. Reactions for specific removal of a defined monomer unit are important.

This monomer distinguishability can arise from an ability to differentiate between label on the various possible monomers in the polymer. As a second means, distinguishability can come from specific reagents which react with particularity on different monomers. Thus, for instance, labels may be used which generally attach to the terminal nucleotide, but whose fluorescent signal differs depending upon the nucleotide. As a third means, a reagent which specifically affects the label on only one monomer may be used, as described below.

In the first example, every polymer cluster will be labeled at a particular end, e.g., the 5' end, without specificity for the monomer located there. The scan step will be able to distinguish the terminal monomers, after which each labeled terminal monomer is specifically removed. The general label step is repeated in the cycle as described.

In the second means for distinguishability, reagents are used which produce a signal which is dependent upon the terminal nucleotide. For example, a labeling molecule which binds only to one specific terminal monomer will provide a monomer specific label. This will provide a cycle much like the first means for distinguishability where the properties of the label is different depending upon the terminal nucleotide to which each specific labeling reagent binds.

In the third means for distinguishability, an individual reagent labels or affects only a specific terminal monomer. Polymers susceptible to each reagent by virtue of terminating with the corresponding monomer will have its label specifically affected. A scan of the matrix after each step and comparison with the earlier scans will determine which positions correspond to polymers ending with a susceptible monomer. Performing a removal step with a second monomer-specific reagent followed by a scan will identify those positional locations having polymer clusters ending with that second monomer. A similar reagent for the other possible monomers will further define all of the possibilities. Finally, when all of the possible monomers have been removed, the labeling reaction may be repeated and the succession of specific reagent and scanning steps will also be repeated. This procedure allows for a succession of automated steps to determine the sequence of the polymer clusters localized to distinct positions.

Finally, a combination of both specificity of reagent and ability to distinguish label on different monomers can be utilized. Neither alone need be relied upon exclusively. Thus, in the case of nucleotides, an ability to distinguish into two separate classes of nucleotides, e.g., A and C from G and T, combined with specific reagents for distinguishing between the indistinguishable label pairs, e.g., in the example provided, A from C, or G from T, can also provide sufficient information for sequencing.

Instead of performing four specific reactions on the same substrate matrix, each of the four individual reactions can be performed on separate parallel matrices. Four separate substrate matrices may be made by a replica plating or successive transfers, each matrix having the same spatial distribution of polymer clusters. Thereby, each separate substrate can be subjected to only a single specific reagent in a highly optimized reaction. On each cycle, one out of the four parallel substrates should show a signal indicating the monomer at the terminal for the cluster at a given matrix position.

Likewise, two parallel substrates can be provided, and each of the parallel substrates is used to determine two of the four possible nucleotides at each position. Instead of treating a single matrix with four separate reactions, this approach allows treating each of two substrates with only two separate reactions. By minimizing the number of reactions to which each chip is exposed, the side reactions will be minimized, the chemistry will be optimized, and the number of cycles through which a matrix will survive will be optimized. This provides an advantage in the number of cycles to which a matrix can be subjected before the signal to noise becomes indistinguishable.

E. Label

The label is important in providing a detectable signal. The signal may be distinguishable among the various monomers by the nature of the signal, e.g., wavelength or other characteristic, as described in Prober et al. (1987) Science 238:336–311. A monomer-specific reagent can allow determination of whether each position has a particular terminal monomer by the presence or loss of label.

The label on the monomer may be attached by a noncovalent attachment, but will be preferably attached by a direct covalent attachment. The label will typically be one which is capable of high positional resolution and does not interfere with the nucleotide-specific chemistry or enzymology. Although many different labels may be devised including enzyme linked immunosorbent assays (ELISA), spectrophotometric labels, light producing or other labels, a fluorescent moiety is the preferred form. For example, an avidin/biotin type affinity binding may be useful for attaching a particular label. Alternatively, an antibody may be used which is specific for binding to a particular terminal monomer. A wide variety of other specific reagents can be used to provide a labeling function. See, for example, U.S. Ser. No. 07/624,114, (a grandchild of which has issued as U.S. Pat. No. 5,800,992) (sequencing by hybridization), which is hereby incorporated herein by reference.

The means of detection utilized will be selected in combination with various other considerations. In some circumstances, a spectroscopic label may be most compatible with a particular monomer. Enzyme linked assays with a spectrophotometric detection system are a workable system. Phosphorescent or light producing assays provide high sensitivity using charged couple devices. Fluorescent systems provide the same advantages, especially where the incident light beam is a laser. The fluorescent label also may provide the added advantage of fluorescing at different wavelengths for the different monomers, providing a convenient means to distinguish between different monomers. Other forms of label may be desired for various reasons, for example, magnetic labels, radioactive labels, heavy metal atoms, optically detectable labels, spectroscopically detectable labels, fluorescent labels, and magnetic labels.

For sequencing nucleic acids by this method, the labeled monomers are simpler than those monomers used for the synthetic method. The blocking group is unnecessary, but terminal specific reagents are more difficult to produce.

The preferred attachment sites will be at the same location as the blocking site, so a combined label and blocking moiety is more preferred. The label will be attached as described, e.g., in U.S. Ser. No., 07/624,114, a grandchild of which has issued as U.S. Pat. No. 5,800,992 (sequencing by hybridization).

Two types of degradation cycles can be used, either non-specific removal of the terminal labeled nucleotide, or a base-specific removal. With the nonspecific removal means, each of the end monomers, when labeled, should be distinguishable from the other three monomer possibilities. This allows for determination of the terminal nucleotide for the cluster localized at a given matrix position. Then the terminal, labeled nucleotides are non-specifically removed and the newly exposed terminal nucleotides will be again distinguishably labeled.

By this scheme, a specific label for each of the different nucleotides may be provided. For example, fluorescent reagents specific for each of the nucleotides may provide a signal with a different wavelength. This will more usually occur when the fluorescent probe is located near the base moiety of the nucleotide In the scanning step, the regions terminating with each of the four different nucleotides may be determined. Then, a reaction is performed removing the labeled terminal nucleotides from all of the polymers. This removal may be either enzymatic, using a phosphatase, an exonuclease or other similar enzyme, or chemical, using acid, base, or some other, preferably mild, reagent. Again, the reactions are performed which label each of the terminal nucleotides and a scan step repeated in the same manner.

In the base-specific removal scheme, nucleotide-specific removal can be performed. For example, an enzyme which will function to remove only a single modified nucleotide, e.g., a 5'-fluorescein-dAMP-specific exonuclease, is constructed. This may be achieved by proper construction of a catalytic antibody. Other similar reagents may be generated for each of the other labeled nucleotide monomers.

Catalytic or derivatized antibodies to catalyze the removal of the 3'-end or 5'-most fluorescent base in a base-specific manner may be constructed as follows. A recombinant antibody library or a series of monoclonal antibodies is screened with fluorescent donor-quencher substrates. These substrates consist of a fluorescent labeled base (A, C, G, or T) on the 5' or 3' end joined by a 5' to 3' phosphodiester linkage to a second base. A collection of all four possible second bases for each of the four end bases gives the best selection target for the required non-specificity with respect to the second base. The second base is then tethered to an acceptor group in sufficient proximity to quench the fluorescence of the end group. In the presence of a catalytic antibody with cleaving activity, a fluorescent signal occurs from the separation of the quenching group from the terminal fluorescent label. To assure both base and end specificity, the positive monoclonal antibody clones are rescreened against the other substrates.

Upon selection of an antibody exhibiting the desired specificity (or lack thereof), the reactive group for cleavage may be attached. This cleavage reagent may be chemical or enzymatic and will be attached by an appropriate length linker to the antibody binding site in an orientation which is consistent with the steric requirements of both binding and specific cleavage.

Particularly useful specific reagents may be produced by making antibodies specific for each of the four different modified terminal nucleotide bases. These antibodies would then specifically bind only to polymers terminating in the appropriate base analog. By combining a cleavage reagent to the specific antibody, a terminal nucleotide specific cleavage reagent is generated.

In one example of the degradative embodiment, all of the polymers may be uniformly labeled at a particular end. Thereafter, a specific removal reaction which removes only a particular nucleotide may be performed, leaving the three other nucleotides labeled. Thereafter, a scanning step is performed through which all regions which had incorporated that particular nucleotide will have lost the label through specific removal. Then, the second specific reagent will be applied which specifically removes the second labeled nucleotide, and the scanning step following that reaction will allow determination of all regions which lose the second particular nucleotide. This process is repeated with reagents specific for each of the last two remaining labeled nucleotides interspersed with scanning steps, thereby providing information on regions with each of the nucleotides located there. Then, the entire process may be repeated by labeling the next terminal nucleotides uniformly. As mentioned below, replication techniques may allow for making four separate but identical matrix substrates. Each substrate may be subjected to single nucleotide-specific reactions, and the scan results correlated with each of the other parallel substrates.

In the degradation scheme, the polynucleotide linkage to the matrix must be more carefully selected such that the free end of the oligonucleotide segments used for attachment will not interfere with the determinations of the target sequence terminus.

F. Utility

The present sequencing method is useful to monitor and check the accuracy and reliability of the synthetic processes described in U.S. Ser. No. 07/362,901 (VLSIPS® parent) and U.S. Ser. No. 07/492,462 (VLSIPS® CIP) (now U.S. Pat. No. 5,143,854). The present method can be used to check the final products synthesized therein, or to label each monomers as they are added stepwise to monitor the efficiency and accuracy of those synthetic methods.

The present invention can also be used to monitor or sequence matrix bound clusters of positionally distinct polymers. This sequencing process provides the capability of simultaneously sequencing a large plurality of distinct polymers which are positionally segregated.

The method will be used to sequence extremely large stretches of polymer, e.g., nucleic acids. A large number of shorter segments of a large sequence can be sequenced with alignment of overlaps either randomly generated, or in an ordered fashion, or particular sequenceable segments of a large segment can be generated. In one approach, a large segment is subcloned into smaller segments and a sufficient number of the randomly generated subclones are sequenced as described herein to provide sequence overlap and ordering of fragments.

In an alternative approach, a large segment can be successively digested to generate a succession of smaller sized subclones with ends separated by defined numbers of monomers. The subclones can be size sorted by a standard separation procedure and the individual samples from a separation device manually or automatically linked to a matrix in a defined positional map. Fractions resulting from size separation can be spatially attached at defined positions, often at adjacent positions. Then polymer sequences at adjacent positions on the matrix will also be known to have ends which differ by, e.g., approximately 25 or 50 or more monomers, thereby providing significantly greater confidence in overlapping sequence data.

III. Specific Embodiments

A specific series of reactions for sequencing a matrix of polynucleotides is described.

A. Synthetic Method

This method involves annealing a primer (common to all the attached sequences by virtue of the cloning construction) near to the 3' end of the unknown target sequences. DNA polymerase, or a similar polymerase, is used to extend the chains by one base by incubation in the presence of dNTP analogs which function as both chain terminators and fluorescent labels. This is done in a one-step process where each of the four dNTP analogs is identified by a distinct dye, such as described in Prober et al. *Science* 238:336–341, or in four steps, each time adding one of the four bases, interspersed with a scanning identification step. When each cluster incorporates the proper one of the four bases and the fluorescence scanning is complete, the matrix is stripped of the label and the chain terminators are deblocked for a next round of base addition. Because the base addition is directed by the template strand, the complementary sequence of the fragments at each address of the matrix is deduced.

(1) Attachment to a Surface.

Both degraditive and synthetic sequencing methods begin by obtaining and immobilizing the target fragments of unknown sequence to be determined at specific locations on the surface.

There are several strategies for photo-directed attachment of the DNA strands to the surface in an orientation appropriate for sequencing. A caged biotin technique, see, e.g., U.S. Ser. No. 07/435,316 (caged biotin parent); and U.S. Ser. No. 07/612,671 (caged biotin CIP), is available. Another technique that is especially applicable for the enzymatic synthesis method is to chemically attach a synthetic oligomer by the 5' end to the entire surface (see FIG. 6), to activate it for photocrosslinking (with psoralen, for example) and to anneal the complementary strands and photocrosslink the target strand of unknown sequence (complementary to this oligonucleotide at the 3' end) at the specific location addressed by light. In this case, the oligonucleotide serves as both the attachment linker and as the synthetic primer. A third method is to physically transfer individual nucleic acid samples to selected positions on the matrix, either manually or automatically.

Many sequences in each step are attached by cloning the library into a series of vectors identical except for the sequences flanking the insert. These primers—can be added at the point of amplification of the cloned DNA with chimeric primers.

Alternatively, sequences are attached to a matrix substrate by colony or phage immobilization. This directly transfers the positional distribution on a petri plate to a usable substrate. Colonies representing a shotgun collection of sequences (enough to assure nearly complete coverage by overlap) are spread over (or in) a nutrient surface at a density to give about 100 or more colonies or plaques in several square centimeters, and the colonies are allowed to grow to about 0.1 mm in diameter (the maximum possible density of clusters at this size is ~10,000 colonies/$cm^2$). As described above, replica platings or successive transfers may allow for preparation of multiple matrices with identical positional distributions of polymers. Each separate matrix may then be dedicated to the reactions applicable to a single monomer.

For example, in the use of a phage library, on a petri dish, the transfer substrate surface is treated to release DNA from the phage. This is done, e.g., with CHCl₃ vapor, SDS—NaOH, or by heating. Prior to release of DNA, the phage particles are often adsorbed to the surface by way of an antibody to the coat protein that has been immobilized on the surface. This strategy prevents diffusion of the phage from the colonies. The matrix surface is prepared by coating with an oligonucleotide, immobilized to the surface by one end that has homology with the phage vector DNA adjacent to the cloning site.

The matrix surface is juxtaposed to the growth surface, and the phage DNA is allowed to anneal to the immobilized oligonucleotide. The growth surface is removed, and the hybrid is stabilized by psoralen or an equivalent crosslinking reagent.

This method provides an efficient one-step method of placing many DNA fragments onto the detection surface in preparation for sequencing. Although the colonies are not placed in predefined locations, the random arrangement of the clusters allows the final sequence to be assembled from correlation of overlap sequence data derived from sequence data derived from each of the defined positions of each target cluster.

Sequences are, in other embodiments, attached by a manual or automated transfer technique. A few cells from each colony in a library is toothpicked into microliter wells. The plate is heated to ~100° C. for a short period to lyse the cells and release the DNA. The plate is cooled and reagents for cycled amplification of the DNA using, e.g., PCR technology, are added, including primers common to all the cloned sequences. See, e.g., Innis et al. (1990) *PCR Protocols: A Guide to Methods and Applications,* Academic Press, which is hereby incorporated herein by reference. The DNA is amplified asymmetrically by unbalanced primer concentration to yield an excess of one strand for sequencing and attached to a substrate by manual or automated means.

An alternative form of automated localization is described above in positioning of a succession of smaller sized polymers which are manually or automatically linked to the substrate in a pattern reflecting sequence overlaps.

(2) Enzymatic Polymerization Method.

The nucleic acid template is, in some embodiments, attached to the surface by either the 5' or the 3' end, usually by a method as described above. A preferred method of attachment is to anneal the template to an oligonucleotide attached to the surface and to crosslink the template to the oligonucleotide. Oligonucleotide primers are usually synthesized chemically. In this case, the immobilized oligonucleotide may also serve as a primer for polymerization. Because polymerization proceeds 5' to 3' on the primer, the template will be attached by its 3' end, or a site 3' proximal to the region to be sequenced, for the purposes of the description to follow.

Step 1: A DNA-dependent, DNA polymerase such as those used for conventional DNA sequencing, for example, Klenow fragment of *E. coli* DNA Pol, Sequenase (modified T7 DNA polymerase), Taq (*Thermus aquaticus*) DNA polymerase, Bst (*Bacillus stearothermophilus*), DNA polymerase, reverse transcriptase (from AMV, MMLV, RSV, etc.) or other DNA polymerases, and the reaction components appropriate to the particular DNA polymerase selected, are placed in the incubation chamber in direct contact with the surface.

Step 2: Fluorescent chain terminators (analogs of dATP, dCTP, dGTP, and TP, each labeled with fluorophore preferably emitting at a distinguishable wavelength) are added to the reaction at a sufficient concentration and under suitable reaction conditions (time, temperature, pH, ionic species, etc., see Sambrook et al. (1989) *Molecular Cloning,* vols. 1–3, and Prober et al.) to cause essentially all of the chains on the surface to be extended by one base and thereby terminated. Detection of the specific label thereby incorporated into each chain identifies the last base added at each positional address in the matrix.

Step 3: The chain termination should be reversible by some means, such as treatment with light, heat, pH, certain other chemical or biological (enzymatic) reagents, or some combination of these. Typically the chain termination results from a blocking moiety which is labile to mild treatment. By one of these means, the blocked 3'OH of the terminating base must be made available for chain extension in the next round of polymerization.

Step 4: There are several suitable labeled, terminator structures as follows:

(a) The fluorophore itself functions as the chain terminator by placement on the 3' hydroxyl through a linkage that is easily and efficiently cleaved (removing the label and leaving the free 3'OH) by light, heat, pH shift, etc. The surface is scanned with a scanning system, e.g., the fluorescence detection system described in U.S. Ser. No. 07/492,462 (VLSIPS® CIP) (now U.S. Pat. No. 5,143,854); and U.S. Ser. No. 07/624,120, a divisional of which has issued as U.S. Pat. No. 5,744,101 (automated VLSIPS®). Then, preferably in a single step, the fluorophore is removed and the chain is activated for the next round of base addition.

(b) The fluorophore is placed in a position other than the 3'OH of the nucleoside, and a different group is placed on the 3'OH of the dNTPs to function as a chain terminator. The fluorophore and the 3' blocking group are removed by the same treatment in a single step (preferably), or they may be removed in separate steps.

(c) An alternative polymer stepwise synthetic strategy can be employed. In this embodiment, the fluorophores need not be removable and may be attached to irreversible chain terminators. Examples of such compounds for use in sequencing DNA include, but are not limited to, dideoxynucleotide triphosphate analogs as described by Prober et al. (1987) *Science* 238:336–341. A second, unlabeled and reversible, set of terminators is also required. Examples of these compounds are deoxynucleotide triphosphates with small blocking groups such as acetyl, tBOC, NBOC and NVOC on the 3'OH. These groups are easily and efficiently removed under conditions of high or low pH, exposure to light or heat, etc. After each round of base addition and detection, the fluorophores are deactivated by exposure to light under suitable conditions (these chains have their labeling moiety destroyed and remain terminated, taking part in no further reactions). The unlabeled, reversible terminators are unblocked at the 3'OH by the appropriate treatment to allow chain extension in subsequent rounds of elongation. The proportion of chains labeled in each round can be controlled by the concentration ratio of fluorescent to non-fluorescent terminators, and the reaction can be driven to completion with high concentrations of the unlabeled terminators.

(d) A single dye strategy is used where all the base analog terminators carry the same fluorophore and each is are added one at a time: A, C, G, T. The addition of each base is followed by scanning detection and labeled. After all four fluorophore are added, reversal of the termination is performed, allowing for the addition of the next base analog. Then, each scanning step determines whether the immediately preceding labeled nucleotide had been incorporated at each distinct position.

The structures of the fluorescent labeled and reversible terminator base analogs are selected to be compatible with efficient incorporation into the growing chains by the particular DNA polymerase(s) chosen to catalyze extension. For example, where two different chain terminators are used, they may be utilized by two different polymerases that are both present during the chain extension step.

Step 5: An optional step is the permanent capping of chain extension failures with high concentrations of dideoxynucleotide triphosphates. This step serves to reduce the background of fluorescence caused by addition of an incorrect base because of inefficient chain extension (termination) at an earlier step.

Step 6: After scanning to determine fluorescence, the fluorophore is removed or deactivated. Deactivation of the fluorophore can be achieved by a photodestruction event. The chain elongation block is reversed (usually by removing a blocking group to expose the 3'OH) by suitable methods that depend on the particular base analogs chosen; and the substrate is washed in preparation for the next round of polymerization.

Step 7: Repeat the cycle.

B. Chain Degradation Method

This method involves labeling the last base of the chain (distal to the surface attachment) with a fluorescent tag followed by base-specific removal. All the polynucleotide clusters on the matrix are labeled using a standard labeling moiety. Base-specific removal of the last base of each chain, interspersed with fluorescence scanning of the array, will reveal the disappearance of fluorescence and hence the identity of the last base of each chain. When all four labeled end bases have been removed, the polymers attached to the matrix are relabeled and the process is repeated, working successively on the DNA chains.

Alternatively, if the label allows distinguishing between different monomers, simpler degradation processes may be employed. A single scan step can distinguish between all four possible terminal nucleotides. The four separate removal steps are then combined into a single nonspecific terminal nucleotide removal step.

The DNA will usually be attached to the substrate by the 3' or 5' terminus depending on the scheme of labeling and cleavage. Because there are well-known 5'-labeling methods, see, e.g., Gait (1984) *Oligonucleotide Synthesis: A Practical Approach,* IRL Press, Oxford, this discussion will assume the 3' end is attached to the substrate with the 5' end free.

Step 1: All the 5'-end bases are labeled with 5'-specific chemistry, e.g., 5' amino linkage to FITC, Nelson et al. (1989) *Nucl. Acids Res.* 17:7179–7186, which is hereby incorporated herein by reference.

Step 2: Scan the matrix to obtain the background level.

Step 3: Optional: Cap all of the labeling failures, e.g., polymers whose ends were not labeled.

Step 4: The terminal A's are removed with end-base, A-specific reagents (such a reagent may be chemical or biological). One example is a 5'-fluorescein-dAMP-specific exonuclease made as a catalytic antibody (see the description above for a scheme of producing this reagent).

Step 5: Scan the matrix to detect those chains that had terminated in A (these will be reduced in fluorescence compared to the fluorescent labeled background).

Step 6: Repeat steps 4 and 5 for each of other three possible bases using the appropriate fluorescein-base-specific cleavage reagent and scan after removal of each of the C's, the G's, and the T's. This succession of steps will allow the determination of the terminal nucleotide of each positionally defined cluster.

Step 7: Relabel the 5' terminal nucleotide of all the new end bases that have been exposed by the earlier rounds of cleavage, and repeat the stepwise removal and scanning processes.

This approach can be extended to protein sequencing using 20 catalytic antibodies (or other amino acid-specific cleavage reagents), each recognizing a terminal amino acid and removing that terminal residue.

The process for sequencing may be summarized as follows for enzymatic polymerization:

1) Target DNA templates (to be sequenced) are attached at positionally defined locations on the matrix substrate.

2) Fluorescent chain terminators are added to a primer under conditions where all polymer chains are terminated after addition of the next base complementary to the template.

3) The matrix is scanned to determine which base was added to each location. This step correlates the added base with a position on the matrix.

4) Chains failing to extend (and therefore to terminate) are capped.

5) The fluorophores are removed or deactivated.

6) The terminators are activated for further chain extension, usually by removal of a blocking group.

7) Steps 2 through 6 are repeated to obtain the base-by-base sequence of many different positionally separated DNA fragments simultaneously.

C. Screening for New Nucleotide Analog/Polymerase Combinations.

The use of a functional combination of blocked nucleotide with a polymerase is important in the synthetic embodiment of the present invention. It is important to ensure that only a single nucleotide is incorporated at the appropriate step. The following protocol describes how to screen for a functional combination.

Test 1. (Test for Polymerase Inhibition)
  In a reaction volume of 20 µl, mix
  1 µg M13mp19 single stranded DNA template
  2.5 ng standard M13 primer (17-mer:
    5'-GTTTTCCCAGTCACGAC-3' (SEQ ID NO:1)
  60 mM tris-CL pH 8.5
  7.5 mM $MgCl_2$
  75 mM NaCl
  Template and primer are annealed by heating to 95° C., then cooling to ~25°
  Extension components are added:
  50 µM (each) dATP, dCTP, dGTP, TTP
  10 µCi P32 dATP
  0.01 µM to 1 mM of the putative terminator compound, further titrations may be desired.
  20 units AMV reverse transcriptase water to 20 µl final volume
  The reaction is run at 42° for about 30 minutes.
  Aliquots are taken at 10, 20, 30 minutes, and samples are TCA precipitated after the addition of 10 µg tRNA carrier.
  The filters are counted for acid-precipitable radioactivity and the mass of dATP incorporated is calculated as a function of reaction time.
  Control reactions are run in parallel consisting of
  A) no added terminator
  B) 10 µM and 100 µM The termination activity of the experimental samples relative to that of ddNTPs is estimated, and a nucleotide is appropriate for further testing if it substantially decreases the number of acid precipitable counts at any time or relative concentration.

Test 2 (Test for Base Specific Termination Activity)

Reactions are run essentially as described by Prober et al. except:
1. Unlabelled primer is used
2. 1 µCi P32 dATP is included
3. No dideoxyNTPs are added to the experimental samples (control reactions containing ddNTP at the usual concentrations, and no test terminators are run in parallel)
4. The test compound is added at a concentration estimated to give 1% and 10% inhibition of incorporation as determined by test #1.

The reactions are run for 10 min at 42°. 100 µM dNTPS are added and the reaction run for an additional 10 min. A portion of the reaction is prepared and run on a sequencing gel in the usual fashion. The ladders obtained with the test compound are compared with that obtained in the ddNTP reactions and the fidelity of the termination activity of the test compound is thereby assessed.

IV. Apparatus

Figure 11:
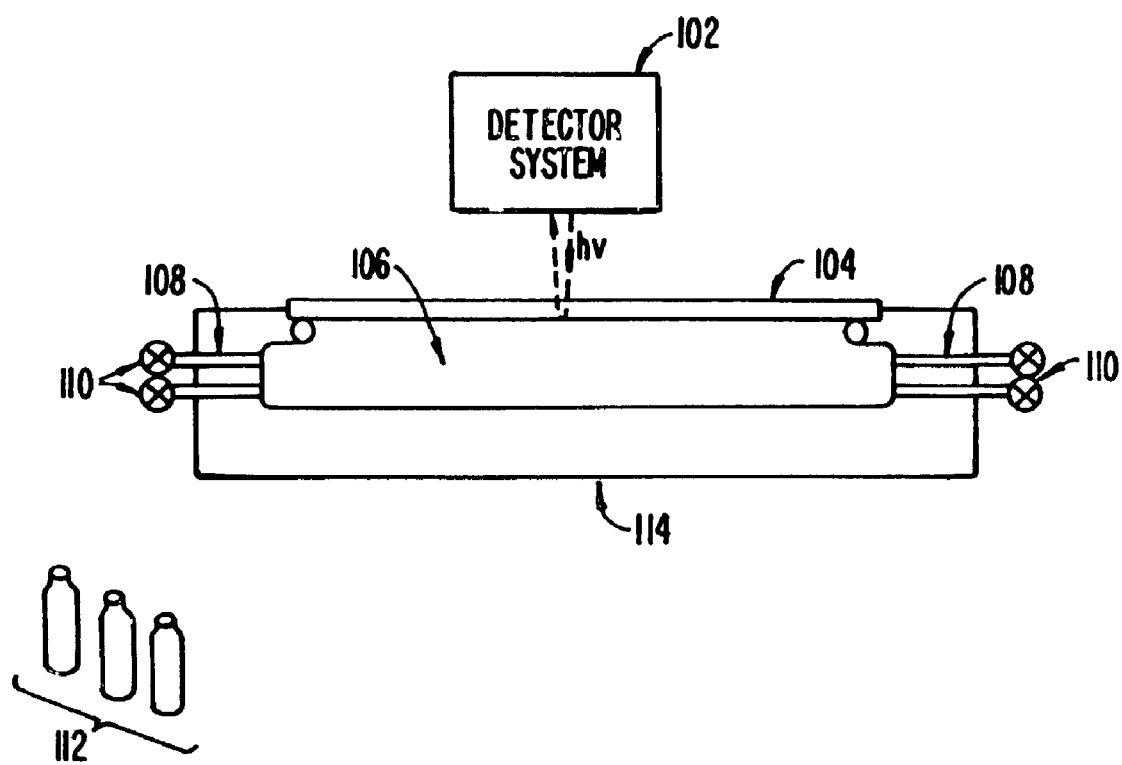
FIG. 11 illustrates a functionalized apparatus for performing the scanning steps and sequencing reaction steps.

The present invention provides a new use for an apparatus comprising a reaction chamber and a scanning apparatus which can scan a substrate material exposed to the chamber. FIG. 11 illustrates a system and a schematized reaction chamber to which is attached a silicon or glass substrate. The system has a detection system 102 as illustrated, in one embodiment, in FIG. 7. A silicon substrate 104, is attached against and forming a seal to make a reaction chamber 106. Leading into and out of the chamber are tubes 108, with valves 110 which control the entry and exit of reagents 112 which are involved in the stepwise reactions. The chamber is held at a constant temperature by a temperature block 114.

All publications and patent applications are herein incorporated by reference to the same extent as if each individual publication or patent application was specifically and individually indicated to be incorporated by reference. The invention now being fully described, it will be apparent to one of ordinary skill in the art that many changes and modifications can be made thereto without departing from the spirit or scope of the claims.

What is claimed is:

1. A method for determining the positions of polynucleotides which terminate with a given monomer, comprising
providing a plurality of different polynucleotides attached at distinct positions of a surface of a support by annealing of the polynucleotides to oligonucleotides immobilized to regions of the surface of the support at a density of at least 1000 regions/cm$^2$, the polynucleotides having terminal monomers labeled in a monomer-type specific manner; and
scanning said surface, thereby determining the positions of said labeled monomer.

2. A method for concurrently determining which subset of a plurality of different polymers attached at distinct positions of a surface of a solid substrate at separable locations at a density of at least 1000 locations per cm$^2$ terminates with a given terminal subunit, said method comprising the steps of:
mixing said solid substrate with a solution comprising a reagent, and thereby selectively marking positionally distinct polymers which terminate with said given terminal subunit; and
determining with a detector which separable locations are marked, thereby determining which subset of said positionally distinct polymers terminated with said given terminal subunit.

3. A method of claim 2, wherein said solution comprises a reagent which marks said positionally distinct polymer with a fluorescent label moiety.

4. A method of claim 2, wherein said terminal subunit is selected from the group consisting of adenosine, cytosine, guanosine, and thymine.

5. A method for determining which subset of a plurality of primer polynucleotides have a predetermined oligonucleotide, wherein the polynucleotides are complementary to and annealed to different template strands which are attached at distinct positions of a surface of a solid substrate at a density of at least 1000 locations per cm$^2$, said method comprising the steps of:
selectively marking said subset of primer polynucleotides having the predetermined oligonucleotide; and
detecting which polynucleotides are marked.

6. A method of claim 5, wherein said oligonucleotide subunit is a single nucleotide.

7. A method of claim 6, wherein the marking comprises elongating said primer with a labeled nucleotide which is complementary to a template.

8. A method of claim 5, wherein the marking step uses a polymerase and a blocked and labeled adenine.

SEQUENCE LISTING

<160> NUMBER OF SEQ ID NOS: 1

<210> SEQ ID NO 1
<211> LENGTH: 17
<212> TYPE: DNA
<213> ORGANISM: Artificial sequence
<220> FEATURE:
<223> OTHER INFORMATION: M13 primer

<400> SEQUENCE: 1
gttttcccag tcacgac                                           17

9. The method of claim 1, wherein the labeled terminal monomers can be distinguished from one another by the wavelength of fluorescent emission.

10. The method of claim 1, wherein the support is a material selected from the group consisting of silicon, glass, ceramics and plastics.

11. A method for determining a subset of polynucleotides which terminate with a given monomer, comprising provinding a plurality of different polynucleotides attached at different positions of a surface of a support by annealing of the polynucleotides to oligonucleotides immobilized to regions of the surface at a density of at least 1000 regions per $cm^2$, the polynucleotides having terminal monomers labeled:

in a monomer type specific manner; and scanning said surface, thereby determining the subset of polynucleotides terminate with a given monomer.

12. The method of claim 11, wherein the labeled terminal monomers can be distinguished from one another by the wavelength of fluorescent emission.

13. The method of claim 11, wherein the support is a material selected from the group consisting of silicon, glass, ceramics and plastics.

14. The method of claim 1, wherein the oligonucleotides are synthesized oligonucleotides.

15. The method of claim 11, wherein the oligonucleotides are synthesized oligonucleotides.

* * * * *